US009956125B2

(12) United States Patent
Bosaeus et al.

(10) Patent No.: US 9,956,125 B2
(45) Date of Patent: May 1, 2018

(54) ABSORBENT ARTICLE COMPRISING A WETNESS DETECTOR

(75) Inventors: Mattias Bosaeus, Kållered (SE); Allan Elfström, Deptford, NJ (US)

(73) Assignee: SCA HYGIENE PRODUCTS, Göteborg (SE)

( * ) Notice: Subject to any disclaimer, the term of this patent is extended or adjusted under 35 U.S.C. 154(b) by 933 days.

(21) Appl. No.: 14/369,763

(22) PCT Filed: Dec. 29, 2011

(86) PCT No.: PCT/EP2011/074229
§ 371 (c)(1),
(2), (4) Date: Jun. 30, 2014

(87) PCT Pub. No.: WO2013/097899
PCT Pub. Date: Jul. 4, 2013

(65) Prior Publication Data
US 2014/0371702 A1    Dec. 18, 2014

(51) Int. Cl.
*A61F 13/15*    (2006.01)
*A61F 13/20*    (2006.01)
*A61F 13/514*    (2006.01)
*A61F 13/42*    (2006.01)
*G01N 27/04*    (2006.01)

(52) U.S. Cl.
CPC ........ *A61F 13/51498* (2013.01); *A61F 13/42* (2013.01); *A61F 13/51484* (2013.01); *G01N 27/048* (2013.01)

(58) Field of Classification Search
CPC ....................................................... A61F 13/42
See application file for complete search history.

(56) References Cited

U.S. PATENT DOCUMENTS

| 4,677,373 A | 6/1987 | Kobayashi et al. |
| 4,768,023 A | 8/1988 | Xie |

(Continued)

FOREIGN PATENT DOCUMENTS

| GB | 1 340 050 | 12/1973 |
| JP | 2002-224093 A | 8/2002 |

(Continued)

OTHER PUBLICATIONS

English language translation of a Decision on Grant dated Nov. 30, 2015 issued in corresponding Russian patent application No. 2014131237 (8 pages).

(Continued)

*Primary Examiner* — Michele M Kidwell
(74) *Attorney, Agent, or Firm* — Drinker Biddle & Reath LLP

(57) ABSTRACT

An absorbent article has a back sheet with an absorbent core disposed on a body side of the back sheet. On a back side of the back sheet, there is provided a substrate carrying a conductive pattern as a liquid discharge detection circuit that is able to be connected to an electric potential generator for performing liquid discharge detection. At least one or a plurality of holes is formed through the back sheet to communicate portions of the conductive pattern with the absorbent core. Longitudinally adjacent pairs of the revealed portions of the conductive pattern form liquid discharge detection zones for detecting liquid discharge in the absorbent core. The detection zones are longitudinally distributed with respect to the absorbent core.

36 Claims, 8 Drawing Sheets

(56) References Cited

U.S. PATENT DOCUMENTS

| | | |
|---|---|---|
| 5,147,345 A | 9/1992 | Young et al. |
| 5,395,358 A | 3/1995 | Lu |
| 7,250,547 B1 | 7/2007 | Hofmeister et al. |
| 7,977,529 B2 | 7/2011 | Bergman et al. |
| 2005/0156744 A1 | 7/2005 | Pires |
| 2008/0243099 A1 | 10/2008 | Tippey et al. |
| 2010/0164733 A1 | 7/2010 | Ales et al. |
| 2011/0263952 A1 | 10/2011 | Bergman et al. |
| 2011/0295619 A1 | 12/2011 | Tough |
| 2013/0018231 A1 | 1/2013 | Hong et al. |

FOREIGN PATENT DOCUMENTS

| | | |
|---|---|---|
| RU | 2125860 C1 | 2/1999 |
| RU | 2385738 C2 | 4/2010 |
| WO | WO 96/14813 A1 | 5/1996 |
| WO | WO 00/00144 A2 | 1/2000 |
| WO | WO-01/006975 A1 | 2/2001 |
| WO | WO 2004/100763 A2 | 11/2004 |
| WO | WO 2006/047815 A1 | 5/2006 |
| WO | WO 2007/038966 A1 | 4/2007 |
| WO | WO-2007/070267 A1 | 6/2007 |
| WO | WO-2008/026123 A1 | 3/2008 |
| WO | WO 2011/054045 A1 | 5/2011 |
| WO | WO 2011/156862 A1 | 12/2011 |

OTHER PUBLICATIONS

English language translation of a Notice of Reasons for Rejection dated Jun. 1, 2015 issued in corresponding Japanese patent application No. 2014-545115 (5 pages).

Communication from the Examining Division dated Aug. 16, 2017 issued in corresponding European patent application No. 11 805 540.9 (6 pages).

Mexican Office Action dated Jun. 27, 2017 issued in corresponding Mexican patent application No. MX/a/2014/007898 (3 pages) and its partial English-language translation thereof (3 pages).

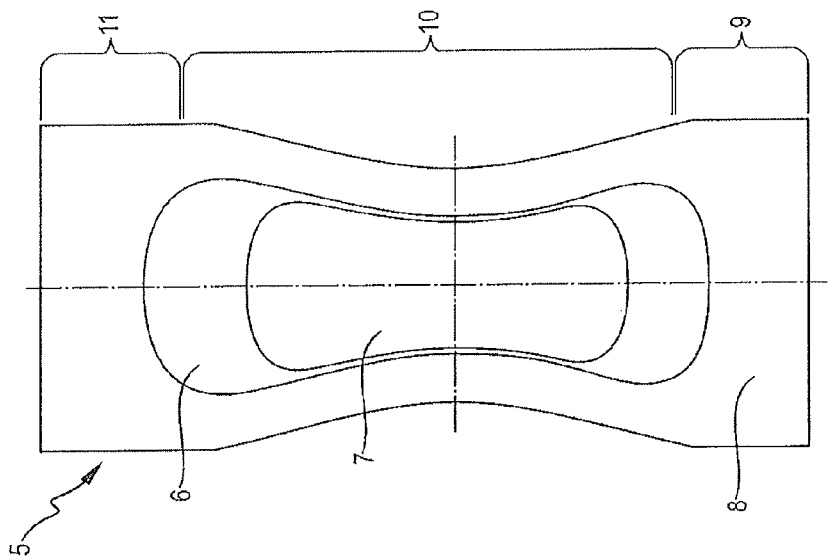
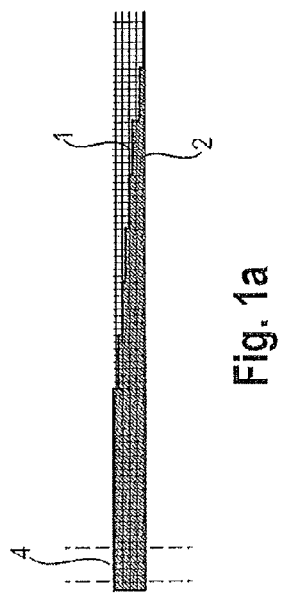

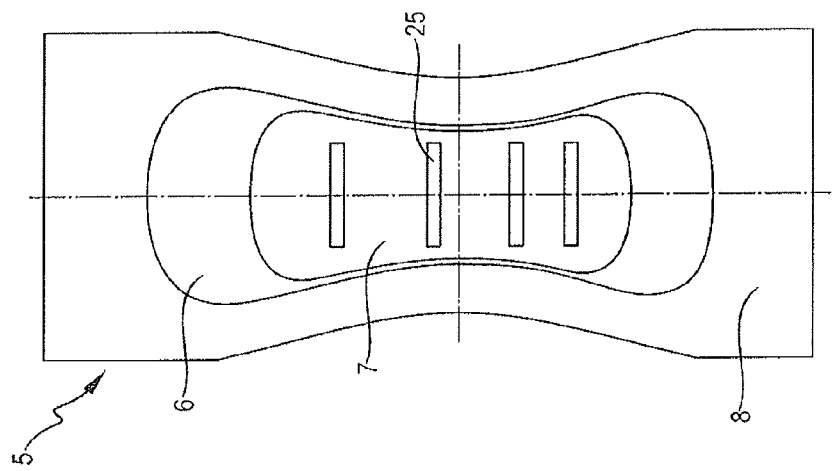
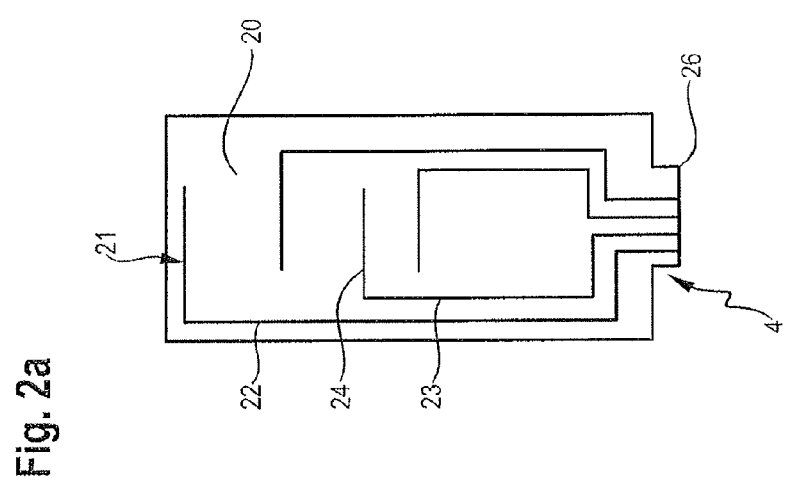
Fig. 2a
Fig. 2b

ABSORBENT ARTICLE COMPRISING A WETNESS DETECTOR

CROSS-REFERENCE TO PRIOR APPLICATION

This application is a § 371 National Stage Application of PCT International Application No. PCT/EP2011/074229 filed Dec. 29, 2011.

TECHNICAL FIELD

The present disclosure relates to an absorbent article including a wetness detector for detecting a liquid discharge of the wearer of the absorbent article.

BACKGROUND

WO 2007/070267 A1 discloses a diaper having first to fourth conductive paths printed or laminated on an inner surface of an outer cover of the diaper. The first conductive path extends longitudinally from a front region of the diaper to a waist region, through a central region and serves as a reference electrode. A conductive pad is disposed at a front waist band end of the first conductive path. The second to fourth conductive paths take on a serpentine form and are respectively located in the front waist region, the crotch region and a rear waist region of the diaper. Leads connect each of the first to fourth conductive paths to respective conductive pads located at a front waist band portion of the absorbent article.

A signalling device is able to attach to the first to fourth conductive pads at the front waist band portion. The signalling device is configured to apply a potential between the first conductive path and each of the second to fourth conductive paths to be able to separately determine the presence of liquid in the front, crotch and rear diaper regions on the basis of liquid bridging the two conductive paths to form a closed circuit.

A problem with the arrangement of WO 2007/070267 A1 is that the leads extending between the serpentine conductive paths and the conductive pads are in electrical communication with the absorbent core. This means that a short circuit can occur between the leads and the first conductive path or reference electrode, which will give an indication that liquid discharge is present in the serpentine path region when, in fact, the trigger is occurring because of liquid discharge at the lead.

It would be desirable to provide an absorbent article with a wetness detector that reduces or eliminates false detections as described above.

In the arrangement of WO 2007/070267 A1, the wetness detector perform wetness detection in a region separated way, but the layout shown requires liquid discharge to sufficiently laterally spread to be present laterally between the first conductive path or reference electrode and the serpentine conductive paths. In such an architecture, the area in which conductive paths are bridged is skewed off-centre, while the area that will be primarily subject to liquid discharge is a longitudinal centre line of the article.

It is desired to offer at least one wetness detector arrangement that is able to perform detection of a longitudinal extent of a liquid discharge and which is not laterally skewed. Also, it is desired for the absorbent article to be convenient to manufacture.

WO 2007/070267 A1 discloses a more simple structure to the serpentine region based conductive paths described above. In this simpler alternative, the absorbent article has two parallel conductive paths extending longitudinally from a front to a rear of the diaper. While reasonably easy to manufacture, this architecture does not allow determination of longitudinal extent of a liquid discharge. What is desired is an absorbent article that is comparably straightforward to make, but which provides longitudinal wetting discrimination.

SUMMARY

In a first aspect, an absorbent article includes an absorbent core for absorbing a liquid discharge, and a plurality of conductive lines disposed on a first, optionally electrically insulating, layer that are partially covered by a second electrically insulating layer, wherein portions of the conductive lines exposed by at least one opening in the second insulating layer are in electrical communication with the absorbent core, thereby providing electrodes for detecting liquid discharge in the absorbent core, and wherein portions of the conductive lines covered by the second insulating layer provide leads extending between each electrode and a control unit attachment area, the second insulating layer ensuring the leads are electrically insulated from the absorbent core. The electrodes are arranged so that a plurality of longitudinally spaced liquid detection zones are provided, each detection zone defined between a pair of electrodes that are electrically isolated from one another when the absorbent core is dry and which are arranged so that when the control unit connects an electric potential to corresponding leads and when the absorbent core is wet, a conductive bridge is formed between the pair of electrodes by the wet absorbent core, wherein a longitudinal axis extends in a front to rear direction of the absorbent article when worn.

The first aspect provides an electrode architecture that can longitudinally discern an extent of a liquid discharge by longitudinally distributing a number of detection zones formed by electrodes that create a conductive bridge between them when the absorbent core is wet. This longitudinal distribution of a number of isolated electrodes means that there will necessarily be a number of longitudinally extending leads. These leads could themselves form conductive bridges between them, which would give misleading detection results. The second insulating layer avoids this problem by preventing such conductive pathways forming between the leads through the wet absorbent core. Further, this architecture is achieved in a convenient to manufacture way, in the form of a laminate structure. There is a design flexibility, as the leads can overlap with the absorbent core without interfering with detection results.

That is, in the first aspect, the absorbent core overlays at least part of the second insulating layer and the underlying conductive lines forming the leads when the absorbent article is laid out flat and viewed in plan from the body side. Further, the absorbent core overlays the exposed portions of the conductive lines forming the electrodes.

In use, when the absorbent article is worn, liquid discharge, such as urine, will pass into the absorbent core and the wet absorbent core will be made into at least partial contact with the second insulating layer and with the electrodes. An electric potential may be applied between electrodes pairs through the corresponding leads, and the liquid discharge in the absorbent core produces a conductive bridge between the electrodes allowing current to flow between them. When the absorbent core is dry, the electrodes are electrically isolated from one another. The second insulating layer prevents current from passing from the leads through the wet absorbent core.

In an embodiment, the at least one opening in the second insulating layer includes at least one hole providing at least one window exposing the conductive lines to the absorbent core to form the electrodes, the at least one window located so that the conductive lines are partly covered by the second insulating layer to form the leads. This arrangement makes it possible to expose the electrodes in an easy to manufacture manner since it only requires a hole to be punched in the second layer.

In an embodiment, the at least one opening in the second insulating layer includes a plurality of holes in the second insulating layer to provide a plurality of windows, one window exposing each of the portions of the conductive lines forming the electrodes. This embodiment provides a frame of insulating material around each of the electrodes, ensuring well defined electrodes in a convenient to manufacture way by appropriately locating the holes.

In one embodiment, the electrodes are elongate and laterally oriented, wherein the leads are elongate and longitudinally oriented. This structure allows one to conveniently define longitudinally spaced detection zones between laterally oriented electrodes. A finer resolution of zones is achievable by increasing the number of longitudinally spaced laterally oriented electrodes. In one embodiment, there are 3, 4, 5, 6, 7, 8 or 9 or more laterally oriented electrodes. In an embodiment, the at least one opening in the second insulating layer includes a plurality of laterally oriented elongate holes forming windows exposing the conductive lines to form each of the electrodes.

In an embodiment, the at least one opening in the second insulating layer includes a plurality of holes in the second layer that form windows exposing portions of the conductive lines to the absorbent core to form each of the electrodes, wherein the windows are longitudinally spaced so as to form respective detection zones between longitudinally spaced electrode pairs.

In one embodiment, there are elongate and longitudinally oriented conductive lines, wherein the electrodes are formed by portions of the longitudinally oriented lines exposed to the absorbent core by the at least one opening in the second layer and the leads are formed by portions of the longitudinally oriented lines covered by the second layer. In an embodiment, the exposed portions are provided by at least one hole forming at least one window in the second layer. In a further embodiment, there is provided a plurality of windows formed by respective holes in the second layer, each window respectively defining an electrode. In this way, the longitudinally separated detection zones can be provided by appropriately exposing portions of the lines with the second layer, which does not require transversely oriented electrodes, which can be more difficult to manufacture. In an embodiment, the lines extend longitudinally on both sides of the exposed portion. This allows for manufacturing tolerance since the exposed portions do not have to be exactly aligned with an end of the lines. In one embodiment, the lines extend from a longitudinal end portion of the first layer to the opposed end portion or from one longitudinal edge to the other. This arrangement is convenient to manufacture as the lines and the first layer can be combined indiscriminately in the longitudinal direction with the exposed portions provided by the second layer defining the location of the electrodes. That is, longitudinal alignment between the first layer and the conductive lines is not required.

In an embodiment, the first and second insulating layers combine to form a liquid impermeable back sheet of the absorbent article. That is, a laminate formed by the first and second insulating layers (including the conductive lines sandwiched therebetween) is liquid impermeable. In this embodiment, the first and second insulating layers form a laminate that can be used as the back sheet of the absorbent core, while the liquid detection zones are integrated in such a laminate.

In a second aspect, an absorbent article includes an electrically insulating back sheet having an absorbent core on a body side of the back sheet and at least one liquid discharge sensor on a back side of the back sheet, and at least one hole in the back sheet communicating the at least one liquid discharge sensor with the absorbent core so that the liquid discharge sensor exhibits a changed electrical property when the absorbent core changes from a dry state to a wet state.

The second aspect uses a hole in the back sheet to electrically communicate the liquid discharge sensor with the core, which means that the liquid discharge sensor can be applied to the back side of the back sheet, which can offer significant manufacturing advantages. An absorbent article can, for example, be manufactured in a regular way and be subsequently modified with at least one hole in the back sheet and a liquid discharge sensor applied from the back side in order to enable the absorbent article for liquid discharge detection. Also, the at least one hole can be designed to select a detection area of the at least one liquid discharge sensor put in communication with the absorbent core. In use, the core and the liquid discharge sensor will contact one another, at least when the core is wet, to allow the liquid discharge sense to sense the wetness state of the absorbent core at the hole. In an embodiment, the hole provides a window.

In an embodiment, the liquid discharge sensor is arranged to have first and second spaced conductive paths communicating with the absorbent core through the at least one hole so that when the absorbent core positioned between the first and second conductive paths changes from a dry state to a wet state, a conductive bridge is formed between the first and second conductive paths that passes through the wet absorbent core.

In an embodiment, the liquid discharge sensor is arranged to have first and second conductive paths communicating with the absorbent core through a hole in the back sheet so that when the absorbent core positioned between the first and second conductive paths changes from a dry state to a wet state, a conductive bridge is formed between the first and second conductive paths that passes through the wet absorbent core in the hole.

In another embodiment, the liquid discharge sensor is arranged to have first and second conductive paths communicating with the absorbent core through respective holes in the back sheet so that when the absorbent core positioned between the first and second conductive paths changes from a dry state to a wet state, a conductive bridge is formed between the first and second conductive paths that passes through the wet absorbent core between the holes.

In another embodiment, there is provided a plurality of liquid discharge sensors and a plurality of holes in the back sheet, each liquid discharge sensor communicating with the absorbent core through at least one hole in the back sheet.

In an embodiment, there is provided a plurality of holes in the back sheet, each hole revealing to the absorbent core an underlying conductive portion of a liquid discharge sensor. In an embodiment, a plurality of the holes, or each of the holes, are longitudinally spaced, wherein a longitudinal axis extends in a front to rear direction.

In an embodiment, there are a plurality of holes in the back sheet and a plurality of electrically conductive paths that are electrically isolated from one another to form the at least one liquid discharge sensor, wherein each of the holes communicate a respective conductive path with the absorbent core so that current is able to flow from the conductive path in one hole to another conductive path in another hole when the absorbent core is wet.

In an embodiment, the back sheet, apart from the at least one hole, otherwise electrically insulates conductive paths forming the at least one liquid discharge sensor from the absorbent core.

In an embodiment, the total area of the at least one hole is less than 50%, 40%, 30%, 20% or 10% of the total area of the absorbent core when the absorbent article is laid out flat and a plan view of the absorbent core is taken. In an embodiment, the total area exposed to the absorbent core of conductive paths or lines making up the at least one liquid discharge sensor is less than 50%, 40%, 30%, 20% or 10% of the total area of the conductive paths when the absorbent article is laid out flat and the absorbent core is viewed in plan. This feature makes it clear that the holes are a minor portion of the back sheet and the holes are minor portions as compared to the full extent of the conductive paths.

In an embodiment, conductive paths forming the at least one liquid discharge sensor are in the form of lines. In one embodiment, there are a plurality of longitudinally extending conductive lines that are laterally spaced from one another, wherein a longitudinal axis is in a front to back direction of the absorbent article. The at least one hole reveals part of each of the conductive lines to the absorbent core. In certain embodiments, there is a respective hole for each longitudinal conductive line. In another embodiment, there are a plurality of spaced longitudinal conductive lines connected to a respective lateral conductive line, the lateral conductive lines being longitudinally spaced from one another, the at least one hole revealing part of each of the lateral conductive lines to the absorbent core. In certain embodiments, there is a respective hole for each of the lateral lines. In an embodiment, each hole reveals part of the lateral line to the absorbent core. The embodiment where the lines run exclusively longitudinally offers an easy to manufacture version of the absorbent core as the conductive lines do not have to be angled relative to a machine feed direction. In the embodiment where there are also laterally extending lines, there is an advantage that a longitudinal progression of liquid discharge through the absorbent core can be reliably followed.

In an embodiment, the at least one liquid discharge sensor is provided by conductive material that is partly communicated with the absorbent core by the at least one hole. There may be a plurality of conductive paths or lines forming the at least one liquid discharge sensor, each of which paths or lines are partly revealed by the at least one hole. In an embodiment, a part of each of a plurality of conductive lines is communicated with the absorbent core by a respective hole in the back sheet. The present embodiments allow the electrical communication with the absorbent core to be achieved in a straight forward way by only partly revealing the conductive material, which provides discrete, well-defined detection zones.

In an embodiment, the at least one liquid discharge sensor is disposed on a carrier sheet or substrate. In an embodiment, the carrier sheet is attached to the back face of the back sheet. The absorbent core is disposed on a front face of the back sheet. In an embodiment, the combination of the carrier sheet and the back sheet provides a liquid impermeable back layer to prevent liquid discharge passing therethrough. Put another way, the carrier sheet covers the holes in the back sheet.

In an embodiment, the back sheet is made of a liquid impermeable material. The back sheet may be the back sheet of a diaper, such as an adult incontinence diaper or a sanitary towel. In an embodiment, the back sheet includes leg contours for fitting with the leg of the wearer. In an embodiment, the back sheet is sized and shaped to include a crotch portion for extending between the legs of a wearer and to front an back waist portions for wrapping around the buttocks and front waist area of the wearer. In an embodiment, the back sheet has a fastening mechanism disposed thereon so that the absorbent article is able to be fastened around the waist of a wearer. In an embodiment, the back sheet forms at least part of an outermost layer of the absorbent article.

In an embodiment, the back sheet forms a substrate for the absorbent core, wherein the absorbent core is positioned within the back sheet when the absorbent article is laid out flat and viewed in plan. In an embodiment, the absorbent core is includes a mixture of absorbent fibres and super-absorbent particles.

In embodiment, the absorbent core also includes a liquid permeable body side liner, wherein the absorbent core is sandwiched between the back sheet and the body side liner.

In an embodiment, the at least one liquid discharge sensor includes at least one pair of longitudinally spaced conductive members that are in communication with the absorbent core through the at least one hole, wherein the pair or longitudinally adjacent pairs of conductive members are longitudinally spaced by a minimum of 0.01 L, 0.02 L, 0.05 L, or 0.1 L and/or by a maximum of 0.5 L or 0.4 L or 0.3 L or 0.2 L, wherein L is a total longitudinal length of the absorbent core when the absorbent article is laid out flat and viewed in plan. This spacing may equally apply to holes revealing respective conductive members. It has been found that such a longitudinal spacing provides sufficiently dense, but not overly so, detection zones.

In an embodiment, a plurality of liquid discharge sensors are distributed longitudinally over at least 0.5 L, 0.6 L, 0.7 L, 0.8 L or 0.9 L, where L is a total longitudinal extent of the absorbent core when the absorbent article is laid out flat and the absorbent core is viewed in plan.

In certain embodiments, the liquid discharge sensor is described as being able to detect a change from a dry state to a wet state of an absorbent core. This is achieved by way of a change in an electrically conductive property as a result of the wet state of the core, and the electrical property change is detected by the liquid discharge sensor. It is also the case that differing degrees of wetness may be detected. Thus, the electrical property will change to a different degree depending upon the degree of wetness in the absorbent core (up to a saturation point). The various forms of the liquid discharge sensor disclosed herein are able to detect not only a dry to wet transition from a relatively drastic change of electrical property, but also a change in the electrical property as a result of the absorbent core becoming more wet.

In a third aspect, a method of making an absorbent article includes forming an electrically conductive pattern on a substrate, forming at least one hole in electrically insulating back sheet material for the absorbent article, providing an absorbent core, and making the absorbent article so that the substrate is disposed on a back side of the back sheet, the absorbent core is disposed on a body side of the back sheet, the absorbent core is disposed on the at least one hole, and so that part of the conductive pattern is revealed to the absorbent core through the at least one hole, whereby current flow is altered between sub-parts of the part of the conductive pattern when the absorbent core changes from a dry state to a wet state.

The third aspect provides a way of making an absorbent article that is readily up-scaled to a factory process. The method includes a hole making step and a step of forming a conductive pattern on a substrate, both of which are able to be performed by a manufacturer in order to make absorbent articles with a high speed output and at an acceptably low cost. Alignment of the holes and the conductive pattern is also a step that the skilled person is able to implement using, for example, marker technology. The resulting absorbent article will conduct a greater current through the absorbent core when the core is wet and the conductive pattern is subjected to an electric potential. The electrically insulating back sheet and the holes means that the current flow zones through the absorbent core can be tailored as desired.

In an embodiment, the wet absorbent core produces a conductive bridge between the sub-parts, which provides a measurable effect on the electrical property as compared to the dry absorbent core. In one embodiment, the sub-parts are parts of the conductive pattern electrically isolated from one another and the wet absorbent core provides a conductive bridge between the electrically isolated parts. In another embodiment, the sub-parts are parts of the conductive pattern that are electrically connected, but the wet absorbent core creates a conductive bridge providing a reduced resistance conduction path.

In an embodiment, the at least one hole is a plurality of holes, each hole revealing a part of the conductive pattern to the absorbent core. In an embodiment, at least some of the plurality of holes are longitudinally spaced along the absorbent core, each of the plurality of holes revealing a part of the conductive pattern to the absorbent core. Longitudinally spaced holes thus reveal sub-parts of the conductive pattern that may be arranged so that longitudinally directed conductive bridges form between them when absorbent core is wet. There may be at least 2, 3, 4, 5, 6, 7, 8 or 9 such holes in the back sheet respectively revealing a part of the conductive pattern.

In an embodiment, the conductive pattern includes a plurality of conductive lines. In one embodiment, the conductive lines are oriented longitudinally and/or laterally with respect to a central longitudinal axis passing through the absorbent core, which is thus elongate, when the absorbent article is viewed in plan and laid out flat. The revealed part of the conductive pattern may be parts of the longitudinal lines or the lateral lines. This linear structure of the conductive pattern provides an easier to manufacture architecture than more complicated designs, while the holes allow the conductive bridges through the absorbent core to be located in an optimal way with respect to design of a liquid discharge detecting circuit.

The part of the conductive pattern revealed to the absorbent core is a minor part, perhaps less than 20% or 10%, of the portion of the conductive pattern overlaid by the absorbent core (when the absorbent article is viewed in plan and laid out flat) but separated from the absorbent core by the back sheet. This feature gives context to the ability of the conductive holes to appropriately select the liquid discharge detection zones in relation to the full coverage of the conductive pattern. Also, the conductive pattern may form leads that are separated from the absorbent core by the back sheet, which means only a minor portion of the conductive pattern would be required to be in communication with the absorbent core. In an embodiment, a portion of the conductive pattern is prevented from forming conductive bridges with the wet absorbent core by the electrically insulating layer so that conductive bridges only extend between sub-parts of the revealed part of the conductive pattern. In an embodiment, the prevented portion is a major portion of the conductive pattern that is located beneath the absorbent core when the absorbent article is viewed in plan and laid out flat.

The substrate may be attached to the back sheet. The attachment may be by an adhesive layer, ultrasonic welding or other known means.

In an embodiment, the combination of the back sheet and the substrate provide a liquid impermeable outer liner of the absorbent article.

In a fourth aspect, a laminate includes a first electrically insulating layer, and a second electrically insulating layer that are laminated together with a plurality of conductive lines sandwiched between the first and second electrically insulating layers, wherein each of the conductive lines are electrically separate from one another, wherein the second electrically insulating layer includes at least one hole to expose a portion of each of the conductive lines, wherein the laminate is such that an absorbent core is able to be placed on the second insulating layer to bring the exposed portions into contact with the absorbent core.

This laminate is able to be fed into a process for making absorbent articles to produce an absorbent article having liquid detection capabilities. The use of such a laminate can make more efficient the process of manufacturing a liquid detecting absorbent article.

In one embodiment, there is provided a plurality of holes in the second insulating layer, each hole exposing a portion of each of the conductive lines. The exposed portions provide electrodes in contact with the absorbent core that are conveniently and well defined by the shape and position of the holes.

In an embodiment, the laminate is elongate and the exposed portions of each of the conductive lines are longitudinally spaced apart. This allows longitudinal discrimination of the location or extent of a liquid discharge.

In an embodiment, there is at least 2, 3, 4, 5, 6, 7, 8, 9 or more conductive lines. There may thus be a corresponding number of holes. Each hole may be longitudinally spaced from the other holes. The more lines and holes there are the more detection zones there can be, which will provide improved detection resolution. Further, even with such a large number of exposed electrodes, the leads are conveniently isolated from the absorbent core by the covered portion of the conductive lines offered by the second insulating layer.

In an embodiment, the laminate is liquid impermeable. This allows the laminate to be used as a back sheet in constructing an absorbent article.

In an embodiment, the conductive lines are longitudinally oriented.

In an embodiment, the conductive lines continue to extend on either side of the exposed portion with respect to a direction of extension of the conductive lines. In another embodiment, the conductive lines extend beyond the exposed portion on either side in a longitudinal direction of the laminate. This feature allows a certain tolerance in the placement of the holes.

In an embodiment, there is provided an absorbent article including the laminate described above as a back sheet and including an absorbent core disposed on a body side of the back sheet so as to cover the at least one hole.

In a fifth aspect, a method of manufacturing an absorbent article includes providing the above described laminate, and forming the absorbent article with the laminate as a back sheet of the absorbent article and arranging an absorbent core on the second insulating layer so that the exposed portions come into electrical contact with the absorbent core and forming the absorbent article including the back sheet and the absorbent core.

In a sixth aspect, an absorbent article includes a plurality of conductive lines extending on an upper side of an electrically insulating layer and in electrical contact with an absorbent core of the absorbent article, wherein the plurality of conductive lines extend through the electrically insulating layer to extend on a lower side of the electrically insulating layer in a first direction, wherein the conductive lines extend transversely on the upper and lower sides of the insulating layer, and wherein respective leads extend longitudinally between each conductive line on the lower side of the electrically insulating layer and a control unit attachment area.

The sixth aspect provides a detection mechanism for liquid discharge in an absorbent core by arranging conductive lines on a side of an insulating layer facing the absorbent core. Each of these lines is connected to a lead insulated from the absorbent core by being provided on a side of the insulating layer facing away from the absorbent core. In this way, current can be applied to a pair of leads from a control unit attached to the control unit attachment area and if the core is wet at the location between the conductive lines, then a current will pass between the corresponding conductive lines through the wet core. If the core is dry, the corresponding conductive lines will remain electrically isolated from one another. A transverse arrangement of the conductive lines requires current to flow longitudinally, which allows a longitudinal extent of a liquid discharge to be determined, particularly if there are a plurality of adjacent pairs of the conductive lines. The leads could potentially interfere with the measurements as they are also longitudinally extending. The leads do not provide stray current paths, however, as they are insulated from the wet absorbent core by extending on the side of the insulating layer facing away from the core. The transverse extension of the conductive lines on the rear side of the insulating layer provides a longer distance over which the longitudinal leads can intersect or cross with them, thereby easing manufacturing.

In an embodiment, the conductive lines and the leads are separately formed and connected.

In an embodiment, there are at least 2, 3, 4, 5, 6, 7, 8, 9 or more conductive lines. In an embodiment, each of the conductive lines are longitudinally spaced from one another.

In an embodiment, the leads are disposed on a substrate and substrate is attached to the lower side of said insulating layer to connect the leads and the conductive lines. Manufacturing is simplified as the transverse lines can be disposed on the insulating layer in one step, the longitudinal leads can be attached to the substrate in another step and the leads and the lines brought together in a third modular step.

In an embodiment, the transverse extension of conductive lines on the lower side of the insulating layer is an increment greater as the longitudinal distance from the control unit attachment area increases. This provides clearance for longer leads going to the transverse lines positioned further away from the control unit attachment area without crossing intermediate transverse lines.

In an embodiment, before the substrate is attached to the insulating layer, the lower side of the insulating layer forms a back outer surface of the absorbent article.

In an embodiment, the transverse conductive lines are conductive threads sewn into the insulating layer to extend through the insulating layer and extend transversely on both sides of the insulating layer. The disclosed construction reduces the complexity of the sewing since the threads do not have to be routed back to the control unit attachment area. The threads may be polymeric thread plated with a conductive (e.g. metal) material or conductive (e.g. metal) wire.

In an embodiment, the leads are coated or printed on a substrate that is attached to the lower side of the insulating layer. Thus, the leads can be connected easily to the lines by using a pre-prepared substrate carrying the leads. The substrate may have conductive foil or conductive ink deposited thereon.

In an embodiment, the substrate forms the control unit attachment area. The substrate can thus be suitably constructed to have the desired material properties (e.g. stiffness) for forming an effective common control unit attachment point.

In an embodiment, the control unit attachment area is in the form of a protruding tab like member.

In an embodiment, the leads converge to the control unit attachment area.

In an embodiment, the leads are provided as longitudinal stripes.

In a seventh aspect, a method of manufacturing an absorbent article includes providing an electrically insulating back sheet having a plurality of conductive units, the conductive units respectively including a conductive portion disposed on a body side of an electrically insulating back sheet, a conductive line disposed and extending on a back side of the back sheet and a conductive path connecting the conductive line and the conductive portion by passing through the back sheet; providing a substrate having a plurality of conductive leads disposed thereon; disposing the substrate on the back side of the back sheet so that the leads respectively connect to the conductive lines on the back side of the back sheet; wherein the absorbent article is made having an absorbent core disposed on the body side of the back sheet so that the conductive portions on the body side of the back sheet are useable to determine a change in electrical property when the absorbent core changes from a dry state to a wet state.

The seventh aspect offers an advantageous manufacturing process in that the conductive lines for detecting liquid discharge in an absorbent core are extending through the back sheet and leads are connected by way of the simple step of appropriately disposing the substrate with respect to the absorbent core. The linear form of the conductive paths on the back side of the back sheet allows the back side conductive paths to appropriately extend for reach the conductive leads. The electrically insulating back sheet allows the leads to be isolated from the core.

In an embodiment, the conductive leads are staggered in length and the conductive lines are staggered in length so that each lead intersects with a conductive line without intersecting with the other conductive lines.

In an embodiment, each lead extends to a common contact area for making contact with a potential generator. In an embodiment, the substrate provides the common contact area. In an embodiment, the substrate protrudes from the back sheet at the common contact area. In this way, the common contact area can be made of a suitable material to which the potential generator is mounted as determined by the substrate. The protruding form provides a flap like common contact area that is easy to attach to the potential generator.

In an embodiment, the conductive portions are electrically isolated from each other when the absorbent core is dry, the conductive lines are electrically isolated from each other and the conductive leads are electrically isolated from each other. In this way, a potential can be applied to each conductive portion through the corresponding lead and line to provide liquid discharge detection zones through combinations of the conductive portions. A conductive bridge is formed between the activated conductive portions when the absorbent core is wet, which is not present when the absorbent core is dry.

In an embodiment, the conductive portions are in the form of conductive lines extending on a body side of the back sheet. In an embodiment, the conductive lines on the body side of the back sheet are of equal length. In an embodiment, the conductive lines on the body side of the back sheet are laterally oriented and longitudinally spaced from each other. This detection architecture has been found to be beneficial in determining volume and frequency liquid discharge data as well as longitudinal spread.

In an embodiment, the conductive lines on the back side of the back sheet are laterally oriented. In an embodiment, the conductive leads are longitudinally oriented. This provides a useful architecture as it allows a common contact area to be provide at a longitudinally separated position with respect to the detection zone, such as at a waistband area of the absorbent article.

In an embodiment, the conductive line, the connecting conductive path and the conductive portion of the conductive units are continuous. In one embodiment, they are formed by conductive thread. The method may include sewing the conductive thread through the back sheet of the absorbent article. The sewing step may be performed from the back side of the absorbent article so that the thread passes from the back side through to the body side of the back sheet. The sewing method allows the liquid discharge means to be retrofitted to an existing absorbent article. The leads are conveniently applied not by sewing but by disposing the substrate appropriately.

In an embodiment, the conductive leads are provided by a layer on the substrate such as a foil, a coating, printing the leads (e.g. using conductive ink). The method may include the step of applying the conductive leads on the substrate. These non-limiting methods for forming the leads allow the conductive leads to be applied in a material efficient manner.

In certain embodiments, the hole (or holes) is (are each) at least 4 mm$^2$, 9 mm$^2$, 16 mm$^2$, 2 cm$^2$, 3 cm$^2$ in area.

BRIEF DESCRIPTION OF THE FIGURES

This and other aspects of the present invention will now be described in more detail, with reference to the appended drawings showing embodiment(s) of the invention, in which:

FIG. 1a shows an intermediate stage of a first embodiment of an absorbent article;

FIG. 1b shows a plan view of the absorbent article of FIG. 1a at a second stage of manufacture;

FIG. 2a shows an intermediate stage of a second embodiment of an absorbent article;

FIG. 2b shows a plan view of the absorbent article of FIG. 2a at a second stage of manufacture;

FIG. 2e shows an exploded view of the absorbent article of FIG. 2a;

DETAILED DESCRIPTION OF PREFERRED EMBODIMENTS

FIGS. 1a-d show an absorbent article and particularly a sequence of manufacturing steps 1a to 1d in making the absorbent article. In manufacturing step 1a, a plurality of conductive leads are provided on a substrate. Each lead extends from a common start position on the substrate and extends by different lengths to a different finishing position. The conductive leads are provided as a coating or printing on the substrate.

In manufacturing step 1b, an absorbent article is provided. The shown absorbent article is an adult incontinence diaper having a liquid impermeable back sheet, a liquid permeable top sheet and an absorbent core disposed therebetween.

In manufacturing step 1c, conductive threads or lines are disposed on a body side of the back sheet and on a backside of the back sheet in a way that passes through the back sheet so that corresponding lines on the body side of the back sheet and on the backside of the back sheet are continuous with one another. When liquid discharge in the absorbent core connects a pair of the conductive lines or threads, particularly an adjacent pair, current can be passed between those conductive lines or threads. In order to apply an electric potential between the pair of conductive lines or threads, the combination of the conductive leads and the substrate provided by manufacturing step 1a is disposed on a backside of the back sheet so that respective conductive leads on the substrate connect to respective conductive lines or threads on the backside of the back sheet.

Figure 1D:
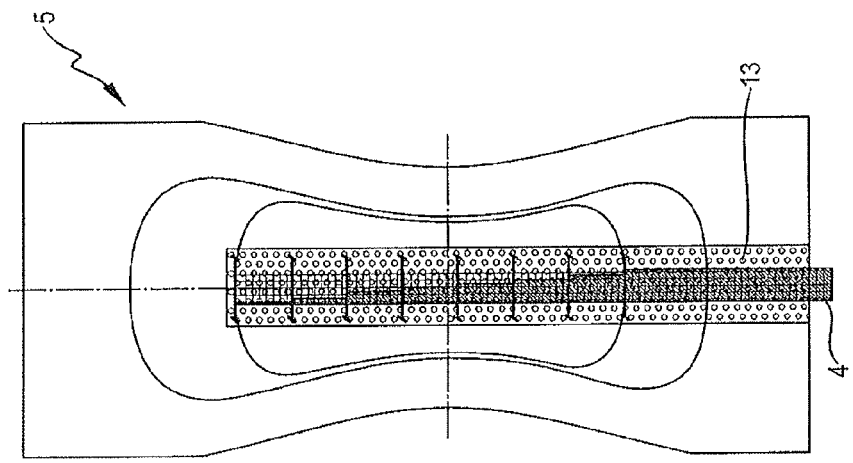
FIG. 1d shows a plan view of the absorbent article of FIG. 1a at a fourth stage of manufacture.
Figure 1C:
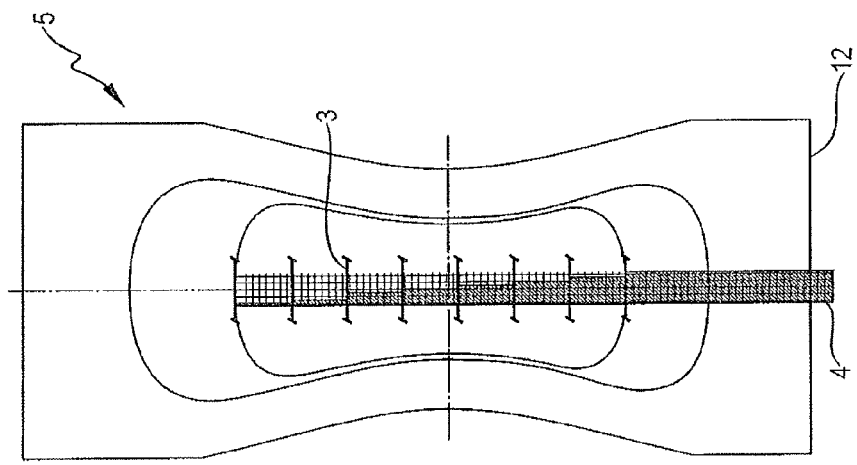
FIG. 1c shows a plan view of the absorbent article of FIG. 1a at a third stage of manufacture.

In manufacturing step 1d, the leads are secured in the position shown in FIG. 1c by adhering a liquid impermeable plastic or non-woven hydrophobic layer over the backside of the substrate so that the liquid impermeable or hydrophobic layer is adhered to both the backside of the substrate and the backside of the back sheet. This outer layer can ensure against leakage from the absorbent article in view of the holes made in the back sheet by passing the conductive threads or lines through the back sheet.

FIGS. 2a-d show manufacturing steps for making an absorbent article that is able to detect liquid discharge in an absorbent core.

In manufacturing step 2a, a conductive pattern is formed on a substrate, where the conductive pattern includes lead portions and detection portions of a plurality of conductive strands. Each lead portion extends back to a common contact area on the substrate. The conductive pattern may be printed, coated or otherwise thinly layered on the substrate.

In manufacturing step 2b, a plurality of through holes are made in the back sheet of an absorbent article. The absorbent article shown in FIG. 2b is an adult incontinence diaper.

In manufacturing step 2c, the substrate provided from step 2a is disposed on a backside of the back sheet so that respective conductive portions of the conductive pattern are aligned with the through holes in the back sheet so as to communicate with the absorbent core in that when an electric potential is applied between a pair of the conductors and the wet absorbent core extends between the conductive portions in the holes, current is then able to flow between the pair of conductive portions.

Figure 2D:
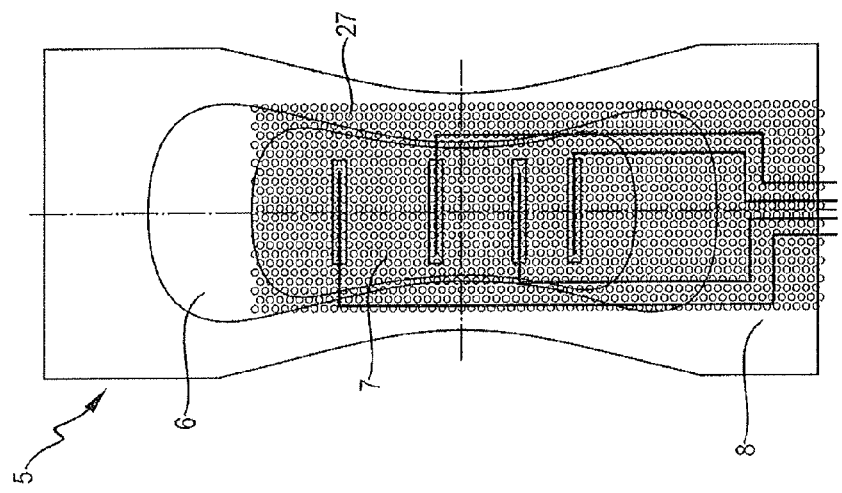
FIG. 2d shows a plan view of the absorbent article of FIG. 2a at a fourth stage of manufacture.
Figure 2C:
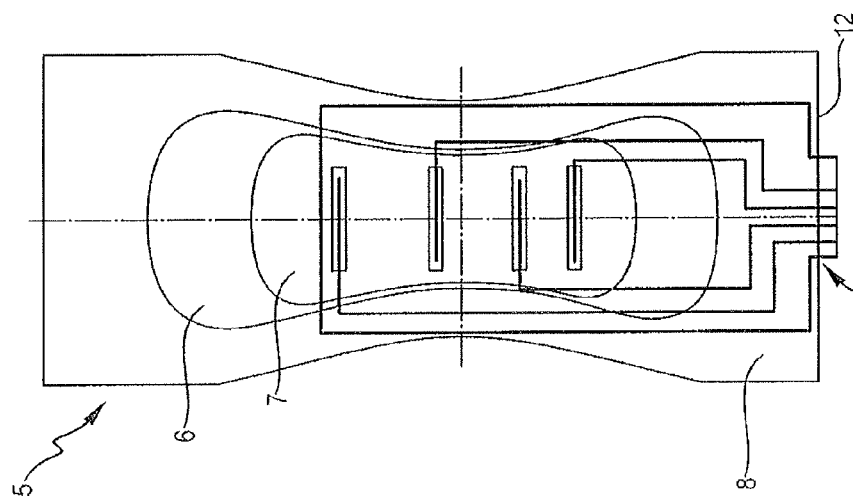
FIG. 2c shows a plan view of the absorbent article of FIG. 2a at a third stage of manufacture.

In manufacturing step 2*d*, the conductive pattern is secured in the position shown in FIG. 2*c* by adhering a hydrophobic non-woven or liquid impermeable layer over the backside of the substrate so as to overlap onto the backside of the back sheet. The liquid impermeable or hydrophobic layer can serve to secure the substrate against the backside of the back sheet, and can also ensure that liquid impermeable integrity of the absorbent article is maintained with respect to the holes formed through the back sheet.

Figure 2E:
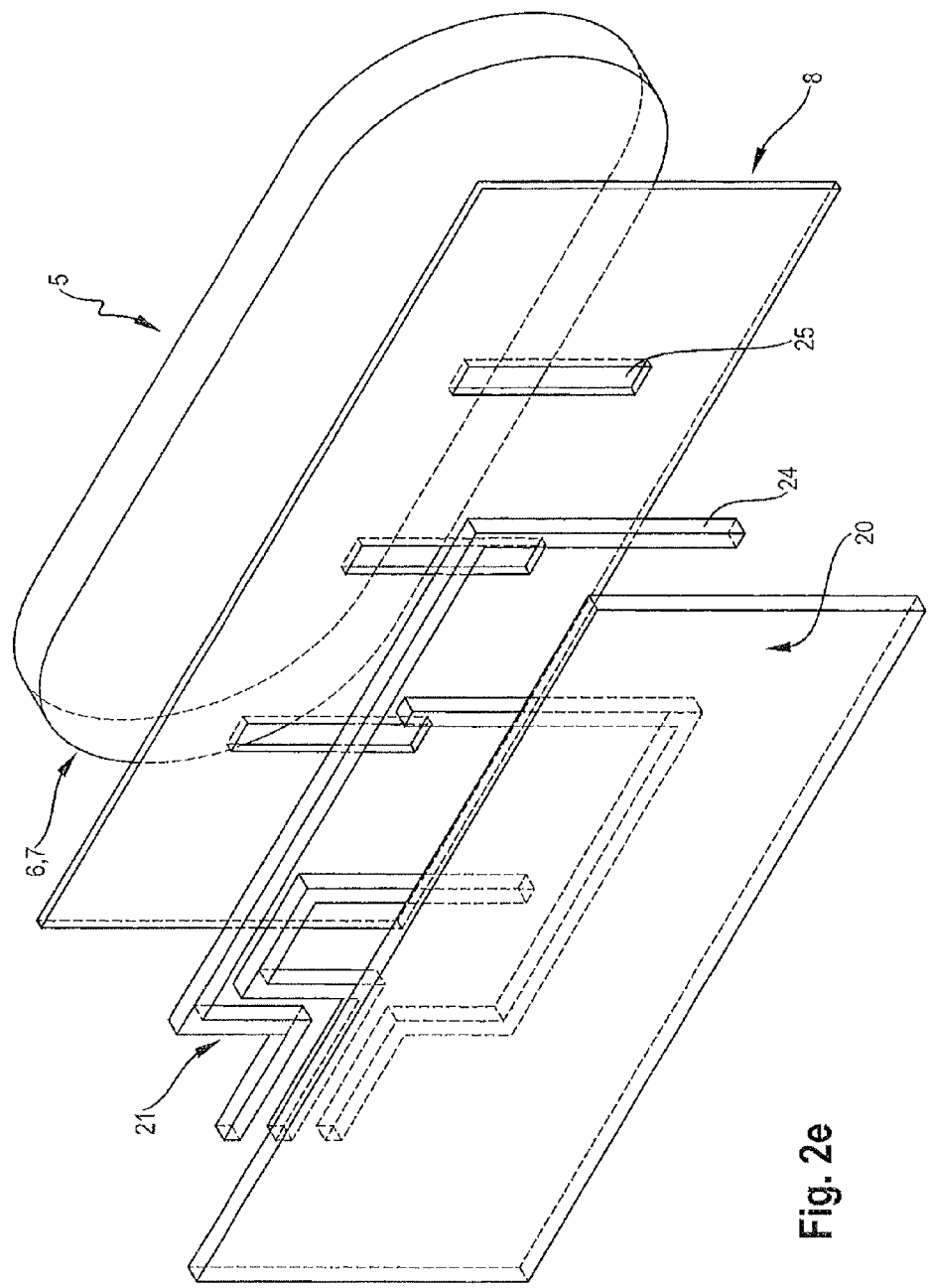

FIG. 2*e* shows an exploded view of the absorbent article of the kind of FIGS. 2*a*-*d* to clearly show how a substrate carrier sheet, an electrical circuit, holes in a back sheet and an absorbent core of the absorbent article are arranged. That is, an electrical circuit for liquid discharge detecting is arranged on a carrier substrate. An absorbent article is disposed on a back sheet and the carrier sheet is arranged relative to the holes so that parts of the electrical circuit are revealed to the absorbent core through the holes. Longitudinally adjacent holes provide liquid discharge detection zones therebetween.

Figure 3:
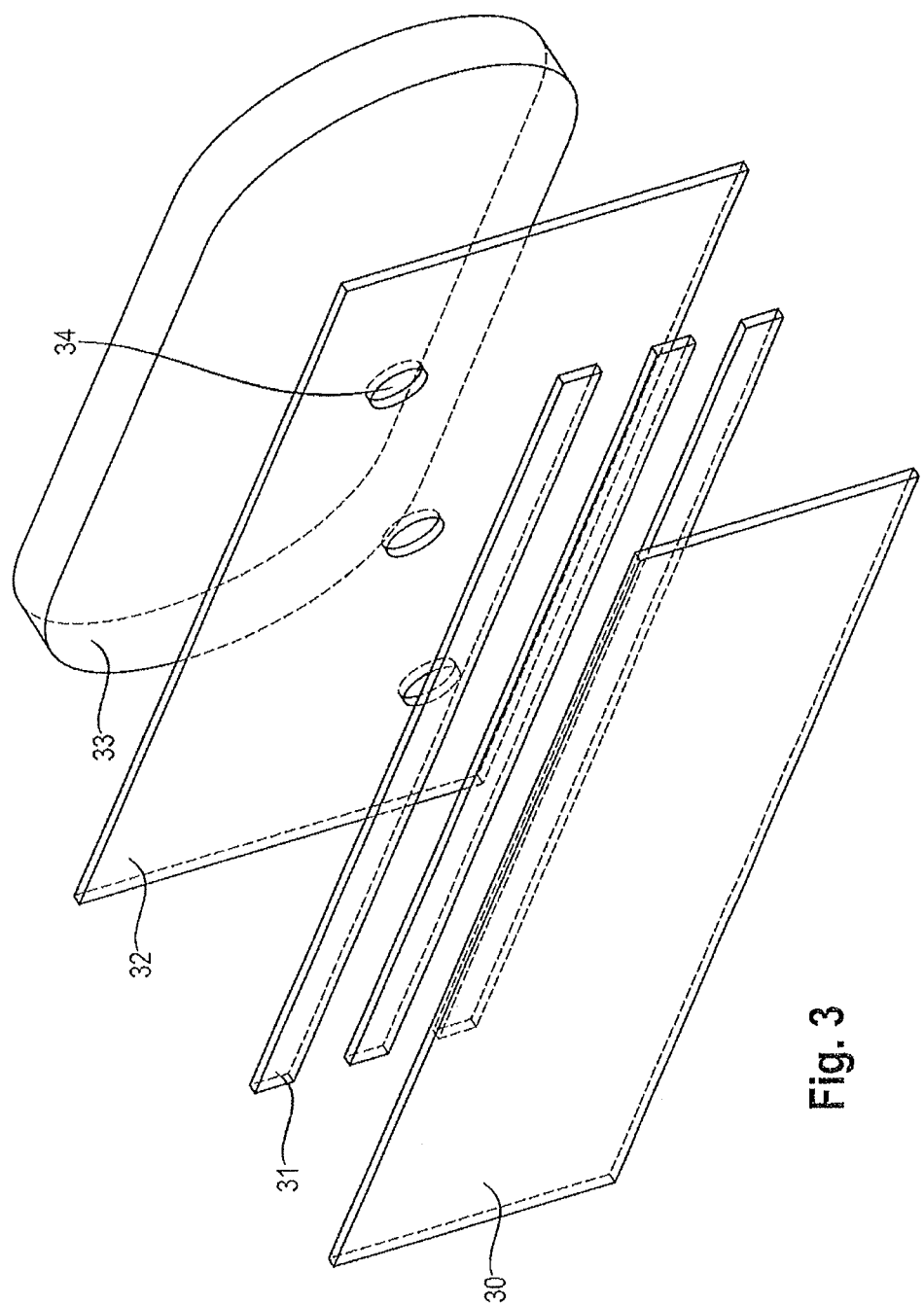
FIG. 3 shows an exploded view of a third embodiment of an absorbent article.

FIG. 3 shows a third embodiment of an absorbent article in which a liquid discharge detection circuit is carried on a substrate and communicated with an absorbent core of the absorbent article through holes formed in a liquid impermeable back sheet of the absorbent article. In the embodiment of FIGS. 2*a*-*e*, the liquid discharge detection circuit disposed on the substrate is in the form of longitudinally extending leads that do not coincide with the holes in the back sheet and laterally extending detection electrodes that coincide with a respective laterally extending hole in the back sheet. FIG. 3 differs in that the liquid discharge detection circuit is provided in the form of longitudinally extending lines, where a portion of each of the longitudinally extending lines is exposed to the absorbent core by a small, in the shown embodiment, circular, hole in the back sheet.

Figure 4:
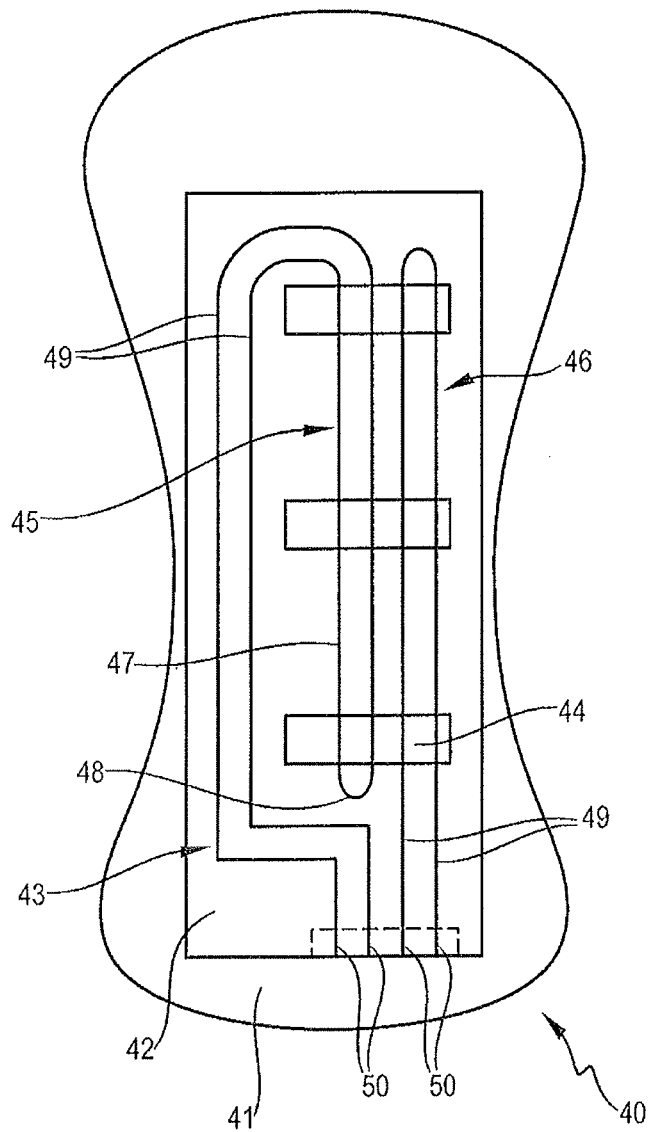
FIG. 4 shows a plan view of a fourth embodiment of an absorbent article.

FIG. 4 shows a fourth embodiment of an absorbent article, in which a liquid discharge detection circuit is disposed on a substrate attached to a backside of a back sheet, where portions of the liquid discharge detection circuit are communicated with the absorbent core through holes in the back sheet of the absorbent article. In the embodiment of FIG. 4, the liquid discharge detection circuit is provided in the form of first and second elongate loops that are oriented longitudinally, with opposed ends of the first and second loops being closed and opposed ends of the first and second loops being open to provide terminal ends. These open loop shapes are thus reverse arranged with respect to one another in the longitudinal direction. A plurality of holes are provided in the back sheet that respectively reveal portions of both the first and second loops to provide discrete detection zones separated in the longitudinal direction.

Figure 5:
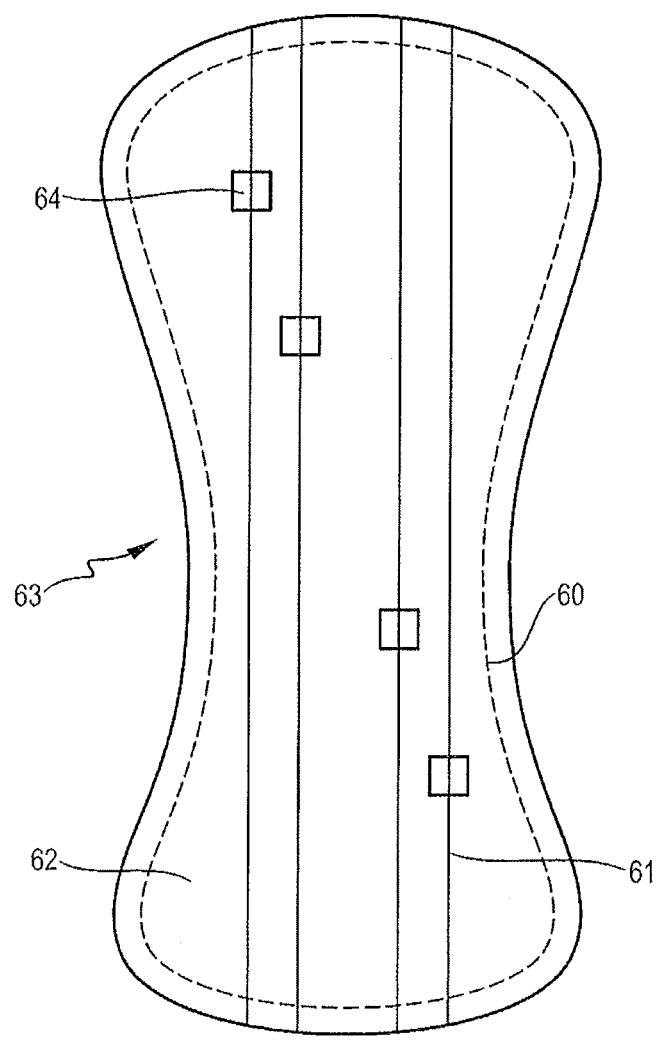
FIG. 5 shows a laminate structure for use in making an absorbent article.

FIG. 5 shows a laminate structure for use in making an absorbent article, particularly a back sheet of the absorbent article. The laminate is liquid impermeable. The laminate includes first and second layers having a conductive pattern disposed therebetween. One of the layers includes a plurality of holes to expose respective portions of the conductive pattern to outside of the laminate so that when an absorbent article is placed over the holes of the laminate, the conductive portions communicate electrically with the absorbent core. In the shown configuration, the conductive lines extend longitudinally and opposed ends thereof terminate at the very longitudinal ends of the laminate structure.

FIGS. 1*a*-*d* show a series of manufacturing steps 1*a* to 1*d* in forming an absorbent article that is able to electronically detect liquid discharge in an absorbent core of an absorbent article.

FIG. 1*a* shows a manufacturing step in which a plurality of conductive leads 2 are disposed on a substrate 1. There are seven leads 2 in the shown embodiment for electrically connecting to a respective detection electrode 3. Other numbers of leads 2 and electrodes 3 could be used, such as two, three, four, five, six, seven, eight or nine or more. The conductive leads 2 extend from a common contact area 4 at one end of the substrate 1 to different longitudinal positions along the substrate 1 that respectively correspond with a longitudinal position of the detection electrodes 3 along an absorbent article 5. The substrate 1 may be in the form of a plastic film or even paper. A purpose of the substrate 1 is to serve as a carrier for the conductive leads 2. The conductive leads 2 may be in the form of metal foil (e.g. aluminium) adhered to the substrate 1 or conductive ink printed on the substrate 1. These forms of the conductive leads are useful as they can be attached to the substrate 1 in a continuous, production line type manufacturing method.

In FIG. 1*b*, the absorbent article 5 is depicted. The absorbent article 5 is a conventional adult incontinence diaper including a back sheet 8, first and second absorbent cores 6, 7 and a top sheet (not shown). The absorbent article 5 is shown in a plan view with the absorbent article 5 laid out flat. The absorbent article 5 includes a front waist region 11, a crotch region 10 and a rear waist region 9 distributed in a longitudinal direction of the absorbent article 5. The first or lower absorbent core 6 is of a larger area than the second or upper absorbent core 7 so that the upper absorbent core 7 forms an island on the lower absorbent core 6. The lower and upper absorbent cores 6, 7 are disposed on the back sheet 8 and sandwiched between the back sheet 8 and the top sheet to form the absorbent article 5. The top sheet is, as the skilled person understands, liquid permeable in order to allow a liquid discharge to pass through it and reach the absorbent core 6, 7, while the back sheet 8 is liquid impermeable to prevent leakage from the absorbent article 5. The absorbent article 5 includes laterally opposed leg contours that are elasticised in order to tightly fit the absorbent article 5 to the legs and buttocks of a wearer. Similarly, front and rear waist band portions are provided that are elasticised in order to tightly conform the absorbent article 5 about the waist of the wearer.

FIG. 1*c* shows the absorbent article 5 associated with the substrate 1 having conductive leads 2 disposed thereon and also with the detection electrodes 3. Turning first to the detection electrodes 3, they are each provided in the form of conductive threads that loop so as to extend laterally along a body side of the back sheet 8, through the back sheet 8 and so as to extend laterally on a backside of the back sheet 8. The loop is open in that the conductive thread does not extend back through the back sheet 8. The liquid discharge electrodes 3 are longitudinally spaced with respect to one another. In the shown embodiment, the liquid discharge electrodes 3 are evenly spaced and distributed longitudinally along the full extent of the upper absorbent core 7. The liquid discharge electrodes 3 are of substantially equal lateral extent and are laterally positioned the same as one another. The liquid discharge electrodes 3 extend to different lateral extents on the backside of the back sheet 8. More particularly, the liquid discharge electrodes 3 have a shorter lateral extent on the backside of the back sheet 8 as the liquid discharge electrodes 3 are more closely positioned with respect to the back waist region 9 in the longitudinal direction. The thread forming the liquid discharge electrodes 3 is looped so that the part of the thread on the backside of the back sheet 8 extends in the laterally overlapping direction with respect to the part of the conductive thread positioned on the body side of the back sheet 8.

The parts of the conductive threads exposed and extending on the backside of the back sheet 8 are physically and electrically connected to the conductive leads by locating the substrate 1 over the backside of the back sheet 8 with the conductive threads 2 facing towards the body side. The substrate 1 is located so that the common contact area 4 protrudes with respect to a back waist edge 12 of the absorbent article 5. This common contact area 4 can be connected with an electric potential generator in order to produce an electric potential between various pairs of liquid discharge electrodes 3. The longest lead extends to the liquid discharge electrode positioned farthest from the rear waist edge 12 and extends in the longitudinal direction past each of the other liquid discharge electrodes 3. The longest lead 2 does not physically and electrically connect with the other liquid discharge electrodes 3 that it passes in the longitudinal direction because each of the preceding electrodes has a lesser lateral extent on the backside of the back sheet 8. Thus, the lateral extent of each of the liquid discharge electrodes 3 is shortened in a stepwise manner from the liquid discharge electrodes 3 positioned farthest away from the rear waist edge 12 to the liquid discharge electrode 3 positioned closest to the rear waist edge 12. Each of the conductive leads 2 extends to a respective liquid discharge electrode 3 but does not physically and electrically connect with any other liquid discharge electrodes 3 because of the space provided by the differing lateral extents of the liquid discharge electrodes 3 on the backside of the back sheet 8.

In FIG. 1c, the substrate 1 is appropriately located on the back sheet 8, but is not yet secured to it as adhesive between the conductive leads 2 and the detection electrodes 3 may hinder electrical conductivity. The manner by which the substrate 1 is secured to the absorbent article 5 in the position shown in FIG. 1c is by way of a further layer 13 that has adhesive disposed on a body side and which comes into contact with both a backside of the substrate 1 and a backside of the back sheet 8 in order to secure the back sheet 8, the substrate 1 and the further layer 13 to the absorbent article 5. The further layer 13 may be a liquid impermeable film, or a hydrophobic non-woven, for example.

The absorbent article 5 of FIG. 1d is used in the following manner. An electric potential generator (not shown) is attached to the common contact area 4 so that respective contacts of the potential generator connect with respective leads 2. An electric potential is generated between various pairs of the leads 2 in order to perform liquid discharge detection. It is envisaged that all combinations of the conductive leads 2 could be activated or the potential generator could limit itself to applying a potential between adjacent pairs of conductive leads 2, which corresponds to adjacent pairs of liquid discharge electrodes 3. In use, assuming an electric potential is applied between adjacent leads 2, the potential is transmitted to the associated liquid discharge electrodes 3 on the backside of the back sheet 8, the potential is transmitted through the back sheet 8 to the body side of the back sheet 8 to thereby apply an electric potential between liquid discharge electrodes 3 in contact with the lower absorbent core 6. If the absorbent core 6 is dry in the region between the activated pair of liquid discharge electrodes 3, then substantially no current will follow between the pair of detection electrodes 3 and the electric potential generator is able to detect this, perhaps by making a resistance measurement. If the lower absorbent core 6 includes a liquid discharge extending between the activated detection electrodes 3, then current is able to flow because of the ions present in the liquid discharge. The flow of current will be able to detected by the potential generator, perhaps through making a resistance measurement.

Each longitudinally adjacent pair of liquid discharge electrodes 3 can be considered to form a liquid discharge detection zone. The potential generator is able to detect which of the zones includes a liquid discharge, thereby allowing a longitudinal extent of the liquid discharge to be determined. The longitudinal extent is particularly useful information as it also enables an estimate to be made of a volume of the liquid discharge. Yet further, a subsequent liquid discharge insult will cause the longitudinal extent of the liquid discharge to change, which will mean that more liquid discharge detection zones are found to include a liquid discharge by the potential generator, thereby enabling the number of liquid discharge insults to be determined. All of this information is useful for diagnostic and research purposes, as well as to a care giver to determine when the absorbent article 5 needs to be changed. Further, the information allows the quality of care to be assessed (e.g. how full the absorbent article 5 is allowed to get before the absorbent article is changed).

In an alternative to the detection electrode architecture of FIGS. 1a-d, the threads could be replaced by separate conductive paths disposed to at least partly overlap with one another on the body side and the backside respectively of the back sheet 8 and to be connected by a conductive via passing from the body side to the backside of the back sheet 8. This would allow the absorbent article 5 to be produced without requiring conductive threads to be sewn into the back sheet 8, which can be time consuming in manufacture, and complicated to carry out other than by hand. Such conductive paths could be formed by printing or laminating conductive ink or conductive foil. Thus, the liquid discharge detection electrodes 3 can be formed by way of printed circuits on each side of the back sheet 8 and connected by conductive vias passing through the back sheet.

Another embodiment is shown in FIGS. 2a-e. In this embodiment, both the leads and the detection electrodes are on a back side of the back sheet, as opposed to the embodiment of FIGS. 1a-d wherein the leads are on the backside of the back sheet and the detection electrodes are on the body side of the back sheet. The description of the various embodiments of FIGS. 2a to 5 does not include further discussion of features already detailed in the above. Reference is made to the above description for common features.

FIG. 2a shows a substrate 20 having a conductive pattern 21 disposed thereon. The conductive pattern 21 includes a plurality of electrically and physically separated conductive lines 22. The conductive lines 22 respectively include a longitudinally extending portion 23 and a laterally extending portion 24. The longitudinally extending portion 23 provides a lead extending from the laterally extending portion 24 to or adjacent to a common contact area 4, at which a potential generator is attached for making contact with each of the conductive lines 22. The laterally extending portion 24 provides a detection electrode for communicating with the absorbent core 6, 7 of the absorbent article 5. The laterally extending portions 24 are longitudinally separated from one another and overlap with one another to a major degree in the lateral direction. The substrate 20 may be a non-woven material or a plastic film. The substrate 20 may be a paper-based material or it may be a plastic sheet. The conductive lines 22 may be formed by printing or coating conductive material on the substrate 20. Thus, the conductive pattern 21 may be formed by conductive ink or conductive foil. The substrate 20 is shaped so as to include a reduced lateral extent tab 26 at one longitudinal end, which serves as the common contact area 4.

In FIG. 2b, a plurality of holes 25 is formed through the back sheet 8. These holes may be preformed in the back sheet 8, which is then assembled into the absorbent article 5 or the absorbent article 5 may be pre-manufactured and the holes 8 subsequently punched or otherwise cut out of the back sheet 8. The holes 25 are formed in relative longitudinal and lateral positions that match with the longitudinal and lateral positions required by the conductive pattern 21 on the substrate 20. The holes 25 are thus evenly distributed in a longitudinal direction and are aligned in a lateral direction. The holes 25 are respectively slot-shaped or elongate, are laterally oriented and have a lateral extent of similar magnitude to that of the lateral portions 24 of the conductive lines 22. The plurality of holes 25 is located longitudinally and laterally within the absorbent core 6, 7 when the absorbent article 5 is viewed in plan and laid out flat.

In FIG. 2c, a manufacturing step is illustrated in which the substrate 20 is associated with the backside of the back sheet 8 so that at least part of each of the lateral portions 24 of the conductive lines 22 are communicated with the absorbent core 6, 7 through a respective one of the plurality of holes 25. That is, the plurality of holes respectively reveals a lateral portion 24 of one of the conductive lines 22 to the absorbent core 6, 7. The substrate 20 is located so that the tab portion 26 protrudes from a rear waist edge 12 of the absorbent article 5 to form a protruding flap for attaching to a potential generator. The potential generator could clamp on the tab portion 26 such as by way of opposing jaws that are movable between open and closed positions. The opposing jaws would include respective contacts for each of the conductive lines 22. In the position of the substrate 20 shown in FIG. 2c, a longitudinally extending portion 23 of the conductive lines 22 are not in physical or electrical communication with the absorbent core 6, 7 because they are not revealed by the holes 25 and are separated from the absorbent core 6, 7 by the back sheet 8. The back sheet thus prevents direct electrical communication between the longitudinally extending portions 23 or leads and the absorbent core 6, 7.

In FIG. 2d, the substrate 20 is secured in position by a further layer 27 that extends longitudinally and laterally beyond the substrate 20 and which is adhered to the backside of the substrate 20 and the backside of the back sheet 8. The further layer 27 may be a hydrophobic or liquid impermeable sheet of non-woven or film material. One purpose of the further layer 27 is to provide liquid impermeability to a backside of the absorbent article 5 with respect to the plurality of holes 25 formed in the liquid impermeable back sheet 8. The further layer 27 thus allows the material of the substrate 20 to be chosen to optimise its conductive pattern carrier function, rather with the design constraint of the substrate 20 having to be made of a liquid impermeable material.

In manufacture, it is envisaged that conventional markers could be used for aligning the lateral portions 24 of the conductive lines 22 with a corresponding hole 25. The conductive pattern 21 on the substrate 20 can be machine manufactured and then associated with the absorbent core 6, 7 in a way that can also be machine implemented, while still allowing the absorbent article 5 to be manufactured in a conventional way. The absorbent article manufacturing process can be modified by the steps of forming holes in the back sheet and associating the substrate 20 with the back sheet in order to convert the absorbent article into a liquid discharge detecting absorbent article. Thus, liquid discharge detecting absorbent articles can be manufactured by machine and at a rate permitting low-cost production.

In use, a potential generator is attached to the tab portion 26 of the substrate 20 so that a respective contact is engaged with a respective conductive line 22. The potential generator is able to apply an electric potential between various combinations of pairs of the conductive lines 22, particularly pairs associated with longitudinally adjacent conductive portions 24. An activated pair of conductive lines 22 will form an electric potential between the associated pair of conductive portions 24. Part of those laterally extending conductive portions 24 are electrically connected with the absorbent core 6, 7 through a respective hole 25 in the back sheet 8. When the absorbent core is dry between the pair of holes 25, substantially no current will flow between the pair of conductive portions 24 exposed to the absorbent core through the pair of holes 25. When the absorbent core 6, 7 is wet so that the web absorbent core extends longitudinally between the activated pair of laterally extending conductive portions 24 exposed by the holes 25, current is able to flow from one of the laterally conductive portions 24 to the other conductive portion 24 via the wet absorbent core in a longitudinally extending conductive bridge formed by the wet absorbent core 6, 7. This current flow can be detected by the potential generator to provide a positive detection of a liquid discharge in a detection zone. The embodiment of FIGS. 2a-e allows a plurality of longitudinally spaced detection zones to be defined between longitudinally adjacent holes 25 in the back sheet.

In the embodiment shown in FIGS. 2a-e, there are four holes and associated laterally extending conductive portions 24, thereby forming three longitudinally spaced detection zones. Other number of holes and laterally extending conductive portions 24 could be implemented, such as three, five, six, seven, eight, nine or more. A three hole embodiment is shown in FIG. 2e. For example, the arrangement of detection electrodes 3 shown in FIGS. 1a-d could be carried over to the embodiment shown in FIGS. 2a-e, thereby providing eight longitudinally spaced laterally extending conductive portions 24 and associated holes 25, longitudinally extending portions 23 and contacts, where the laterally extending portions 24 would be equally spaced in the longitudinal direction and arranged in the same way as that shown in FIGS. 1a-d.

FIG. 2e shows an exploded view of an absorbent article 5 of the same kind as described above with respect to FIGS. 2a to 2d in that a back sheet includes laterally oriented slots, these slots reveal to an absorbent core 6,7 laterally extending parts 24 of a conductive pattern 21 and the conductive pattern is disposed on a substrate 20. In the version of FIG. 2e, there are three longitudinally distributed holes 25 and revealed parts 24 of the conductive pattern 21, thereby forming two longitudinally spaced liquid discharge detection zones between longitudinally adjacent pairs of the revealed parts 24.

FIG. 3 shows a third embodiment in which a back sheet 32 is provided with a plurality of holes 34 in order to communicate part of respective conductive members 31 underlying the back sheet 32 with an overlying absorbent core 33.

The back sheet 32 is of a conventional, liquid impermeable kind. The back sheet 32 may be formed by a plastic film or by a hydrophobic non-woven material. The back sheet 32 has a plurality of holes 34 formed through the back sheet 32. The holes 34 are longitudinally spaced from one another with respect to a longitudinal axis of the absorbent article. Further, the holes 34 are laterally spaced with respect to one another. In this way, a line connecting each of the holes 34 extends diagonally with respect to the longitudinal axis.

An absorbent core 33 is disposed on a body side surface of the back sheet 32. The absorbent core 33 is also of a conventional kind, which is usually formed from a mixture of air laid absorbent fibres and super absorbent polymer particles or fibres. The absorbent core 33 is positioned so as to cover all of the holes 34.

On a backside of the back sheet 32, there is provided a plurality of conductive members 31. Each conductive member 31 is provided in the form of a strip of conductive material. The conductive members 31 are elongate and longitudinally oriented. They extend from one longitudinal edge of the back sheet 32 to the opposed longitudinal edge of the back sheet 32. Each conductive member 31 is located so that it covers one of the holes 34, thereby providing a path for electrical current passing from one of the conductors 31 through the associated hole 34 into the absorbent core if the absorbent core is wet where the associated hole 34 is positioned. The holes 34 respectively reveal only a small portion of the conductors 31 to the absorbent core 33. The holes 34 are respectively of comparable dimension to the associated conductive members 31 in the lateral direction, while being significantly smaller than the conductive members 31 in the longitudinal direction.

A substrate or carrier sheet 30 is provided over a backside of the conductive members 31 so as to completely cover the conductive members 31 and attach to a backside of the back sheet 32. The substrate 30 is made of a liquid impermeable material so as to ensure that the liquid discharge cannot leak out of the absorbent article from the absorbent core 33 through any one of the holes 34.

FIG. 3 shows only part of the absorbent article. The back sheet 32 is bigger than that shown so as to also define front and rear waist regions for extending around the waist of the wearer and also leg region contours including leg elastics associated with the leg contours for securing the absorbent article to a user. Further, a top sheet will be positioned on the body side of the back sheet 32 so that the absorbent core 33 is sandwiched between the top sheet and the back sheet 32. These are conventional features of an absorbent article and do not need to be described in detail herein.

In use, a potential generator is placed into contact with the conductive members 31 so that a respective contact of the potential generator contacts a respective conductive member 31. In this way, the potential generator is able to act on various pairs of the conductive members 31 to apply an electric potential between the pair. In the case of the absorbent core 33 being dry in a space between the pair of holes 34, the potential generator would detect relatively zero current flow between the pair of associated conductive members 31, whereas if the absorbent core 33 is wet along the space a relatively large current flow will be able to be detected by the formation of a conductive bridge extending through the wet absorbent core 33. Thus, a straight line extending between pairs of holes 33 can be considered a detection zone and the arrangement of FIG. 3 allows the potential generator to determine whether the absorbent core 33 is wet in a plurality of detection zones, where these detection zones are longitudinally spaced from one another as a result of the plurality of holes 34 being longitudinally spaced from one another.

It can be seen from FIG. 3 that the absorbent article does not necessarily have to be made first and then provided with liquid discharge detection capability. It can be envisaged by the skilled person that substrate material could be provided in a method of manufacture, back sheet material 32 could be provided, the holes 34 could be formed in the back sheet material and the substrate 30 and back sheet 32 could be attached together with the conductive members 31 disposed therebetween and positioned appropriately so as to cover a respective one of the holes 34. After this, the remaining features of the absorbent article could be manufactured, including providing the absorbent core 33 on the body side of the back sheet 32 and sandwiching the absorbent core 33 between a top sheet and the back sheet 32. A similar manufacturing method is applicable to the embodiment of FIG. 2 in that the substrate 20, the conductive pattern 22 and the back sheet 8 with the holes 25 formed therein could first be provided and then the remainder of the absorbent article subsequently made including disposing the absorbent core 6, 7 on a body side of the back sheet 8.

In the present embodiment, the holes 34 are substantially circular. Other shapes for the holes 34 could be used, such as squares, triangles, etc, when the back sheet 32 is viewed in plan. It is further envisaged that correspondingly shaped and sized holes could be applied to the embodiment of FIGS. 2a-e so that the embodiment in FIGS. 2a-e would not have laterally oriented slot-shaped holes 25, but would instead have holes that are sized to be significantly smaller in the lateral direction so as to uncover only a minor portion of the laterally extending parts 24 of the conductive pattern 24. In such a variation of the embodiment of FIGS. 2a-e, the holes could be aligned along a common longitudinal axis, particularly a central longitudinal axis.

In the embodiments of FIGS. 2a-e and 3, the shortest straight line between the holes 34 extends through back sheet material. That is, the holes 34 are longitudinally spaced and connected in the longitudinal direction by the back sheet material, which ensures that the current must pass through the back sheet into the absorbent core and back through the back sheet, so as to avoid any direct leakage currents between the conductive liquid discharge electrodes.

In another variation of the embodiment of FIG. 3, the conductive members 31 could be provided in the shape of wires or lines, rather than flat, strip-shaped material as shown in FIG. 3. Likewise, the line or wire form for the conductive pattern 21 of the embodiment of FIGS. 2a-e could instead be provided by flat, strip-shaped conductive material. In all of the embodiments, the conductive paths could be provided by way of conductive foil, conductive ink or wire, and could be disposed on the substrate 30 of the back sheet 32 by printing, coating, adhering, etc.

In the embodiment of FIG. 3, there is shown three holes 34 and three conductive members 31. In an alternative embodiment, there could be a greater number of conductive members 31 and associated holes 34, such as four, five, six, seven, eight, nine or more. The more conductive members 31 and associated holes 34 that are provided, the greater is the resolution in determining the location and extent of any liquid discharge in the absorbent core 33. The trade-off for this greater accuracy is increased material costs in terms of providing more conductive members, reduced integrity of the back sheet because of the increased number of holes, and increased circuit complexity in the potential generator. In another alternative, two conductive members 31 and associated holes 34 could be provided.

FIG. 4 shows a fourth embodiment in which holes in a back sheet of an absorbent core are used to communicate underlying conductive paths with an absorbent core. The absorbent article 40 includes a back sheet 41 and a substrate 42 applied on a backside of a back sheet. Sandwiched between the back sheet 41 and the substrate 42 is a conductive pattern for liquid discharge detection. The absorbent core and top sheet on the body side of the back sheet 41 is not shown in FIG. 4 for clarity purposes. Alternatively, reference numeral 40 could be considered to be directed to a laminate of a back sheet 41 and a substrate 42 with a conductive pattern 43 disposed therebetween that forms a pre-cursor for forming an absorbent article when combined with the absorbent core and top sheet.

The back sheet 41 and the substrate 42 have been described in the embodiments previously and this disclosure is applicable to the present embodiment. The embodiment of FIG. 4 differs from the preceding embodiments, particularly the embodiments of FIGS. 2*a-e* and 3, in the relative arrangement of the holes 44 in the back sheet 41 and the underlying conductive pattern 43. The conductive pattern 43 includes two separate circuits 45, 46. The first and second circuits 45, 46 respectively include loop parts 47, each loop part 47 has a closed end 48 and an open end 49 so that the loop part 47 is in the shape of an open loop when the absorbent article is laid out flat and viewed in plan. The first and second circuits 45, 46 are reverse oriented relative to one another, so that the closed ends 48 of the loop parts 47 are positioned in longitudinally opposed parts of the absorbent article 40. From the closed end 48, the first loop 45 extends longitudinally in a rear to front direction, while the remaining portion of the loop part 47 of the second circuit 46 extends in a front to rear direction relative to the closed end 48.

The first and second circuits 45, 46 also include lead parts 49 and contact parts 50 connected to the loop part 47. The leads 49 extend from the open loop part 47 to a common contact area in a rear waist portion of the absorbent article 40. In the shown embodiment, the common contact area, within which the contacts 50 are disposed, is provided as a flap within the footprint of the back sheet 41 when the absorbent article is laid out flat and viewed in plan. This may also be provided in the form of a protruding flap relative to a rear waist edge of the back sheet 41 as in the embodiments of FIGS. 1*a-d* and 2*a-e*. The first and second circuits 45, 46, respectively include a pair of contacts for respective receipt of active and return poles of a potential generator so that current can be caused to flow around the loop part 47.

The holes 44 formed through the back sheet 41 are longitudinally spaced apart and distributed evenly in the longitudinal direction. The holes 44 are shaped in the form of laterally oriented slots that are disposed so as to respectively reveal parts of the loop part 47 of both the first and second circuits 45, 46. In particular, the holes 44 uncover outward and return legs of the open loop part 47 of laterally adjacent parts of the first and second circuits 45, 46.

In use, a potential generator is applied at the common contact area so that respective contacts of the potential generator make contact with contacts 50 of the first and second circuits 45, 46. A potential applied between the pair of contacts of the first circuit causes current to flow around the circuit 45 and particularly around the open loop part 47. If the overlying absorbent core is wet so as to connect outward and return legs of the open loop part 47, then a short circuit will form so that substantially all of the current does not flow around the full loop and instead flows through a reduced loop created by the short circuit. This reduced resistance path is detectable by the potential generator and the extent of the reduced resistance is indicative of where, in the longitudinal direction, the short circuit occurred. More specifically, the potential generator is able to determine whether the short circuit occurred at hole 1, hole 2 . . . hole n of the plurality of holes 44, with each consecutively numbered hole being spaced from the preceding hole in the longitudinal direction. Thus, the first circuit 47 allows a longitudinal extent of a liquid discharge in the rear to front direction to be determined.

The second circuit 46 works in the same way, but because it is reverse arranged in the longitudinal direction relative to the first circuit 47, a longitudinal extent of the liquid discharge can be detected in the front to rear direction. The first and second circuits 45, 46 thus allow opposed longitudinal extents of any liquid discharge in the absorbent core to be ascertained by the potential generator, which gives an indication of the overall area and position of the full liquid discharge. Imagining a liquid discharge overlying the first and second holes 44 closest to the contacts 50 as shown in FIG. 4, current would be caused to short circuit in the hole closest to the contacts 50 in the second circuit 46, and current will be caused to short circuit in the second hole from the contacts 50 in the longitudinal direction, thereby allowing the potential generator to determine that the liquid discharge covers these two holes, and so has at least this longitudinal extent, but not so much of a longitudinal extent as to the third hole.

The potential generator may include a series of resistance values for the first and second circuits 45, 46 in a memory as reference values for making a comparison with the measured resistance. The stored resistance reference values will correspond to resistance measurements expected if the full circuit is traversed, if a short circuit occurs at hole 1, hole 2 . . . hole n, where each of these holes are successively further away in the current carrying direction from the pair of contacts for the particular circuit 45, 46. The potential generator can thus make a comparison between the measured resistance value and the reference values to determine at which of the holes 44, and thus the longitudinal location, that the short circuit occurred. When this information is determined for both the first and second circuits 45, 46, the longitudinal extent of the liquid discharge of the absorbent core is able to be determined.

In the embodiment of FIG. 4, the holes 44 are slot-shaped and laterally oriented, so as to uncover the outward and return legs of both the first and second circuits 45, 46. An alternative arrangement could be provided in which the holes 44 are each split into two or four holes, which are laterally spaced with respect to one another, where each of these groups of two or four holes are longitudinally spaced in the same way as the slot holes 44 of FIG. 4. In the two laterally spaced holes scenario, the first of these holes will uncover outward and return legs of the first circuit 45, and the second of these holes will uncover outward and return legs of the second circuit 46, where the uncovered portions are laterally spaced and longitudinally aligned. In the four holes scenario, the first hole will uncover a part of an outward leg of the first circuit, the second hole will uncover a return leg of the first circuit, the third hole will uncover an outward leg of the second circuit and the fourth hole will uncover a return leg of the second circuit 46. These four holes will be laterally spaced, but longitudinally aligned. A number of these groups of two or four holes will be longitudinally spaced to achieve an architecture according to the principles described above with respect to FIG. 4. The use of split holes in this way may allow an integrity of the back sheet 41 to be increased as compared to the larger holes shown in FIG. 4, but a trade-off for this advantage is increased manufacturing complexity, particularly in aligning each hole with the legs or respective legs of the first and second circuits 45, 46.

In a further alternative to that shown in FIG. 4, the holes 44 could be unevenly distributed. It could be advantageous to concentrate the holes 44 at an area of the article most likely to receive liquid discharge and to have the holes 44 less concentrated at other areas. That is, the longitudinal distance between holes 44 could be less at an expected urination receipt area and the holes 44 could be spaced further apart longitudinally outside of the expected urination receipt area. Such a non-uniform distribution of the liquid discharge detection parts to concentrate the liquid discharge detection parts at an expected liquid discharge area of the absorbent core as compared to other areas of the absorbent core is applicable to all of the embodiments disclosed herein.

In the embodiment of FIG. 5, a laminate is illustrated that comprises a substrate 62 and a back sheet 60 with conductive lines 61 sandwiched therebetween. The conductive lines 61 extend from one longitudinal edge to the opposed longitudinal edge of the laminate 63. The conductive lines 61 are electrically and physically separated from one another. The conductive lines 61 are spaced in a lateral direction. The back sheet 62 includes a plurality of holes 64. The holes 64 respectively uncover a discrete portion of the conductive lines 61 so that when the laminate 63 is formed into an absorbent article, the absorbent core will be positioned to cover the holes 64. The holes 64 are longitudinally distributed so that each hole 64 is longitudinally spaced from the other holes 64 to provide liquid discharge detection zones between longitudinally neighbouring holes 64.

In use, numbering the conductive lines 61 in order from the left-hand side in FIG. 5 as lines 1, 2, 3 and 4, respectively, an electric potential is applicable between the first and second lines to activate a first pair of the lines and an electric potential can be applied between the second and third lines to activate a second conductive pair of the lines 61. An electric potential is also applicable between the third and fourth conductive lines 61 to provide a third conductive pair of the lines 61. Each pair of conductive lines 61 is associated with a liquid discharge detection zone between longitudinally adjacent holes 64. The zones are longitudinally distributed. In the event of the absorbent core being dry, substantially no current will be detected extending between the first to third pair of conductive lines 61. In the event of a wet absorbent core that is located so as to connect the holes 64 associated with the first pair of conductive lines 61, current is able to flow, which can be determined by the potential generator, thereby indicating that liquid discharge is present in this detection zone. Likewise, if a liquid discharge connects the holes 64 associated with the second or third pair of conductive lines 61, then a determination can be made that a liquid discharge is present at the longitudinal location of the second or third detection zone.

Such detection zones formed by a pair of holes revealing a part of a pair of electrically separate conductors could be distributed longitudinally throughout the portion of the back sheet 60 that is to come into contact with an absorbent core. For example, three, four, five, six, seven, eight or nine or more of such detection zones could be provided. Of course, the more detection zones that are provided, the more conductive lines 61 that there is to be incorporated into the laminate 63 and also the greater number of contacts that must be made with the potential generator, which can increase complexity and manufacturing cost.

The laminate 63 of FIG. 5 can be advantageous in terms of manufacturing. Material for forming the substrate 62 can be fed, along with material for forming the conductive lines 61 and material for forming the back sheet 62 in a machine direction. These three streams of material can be brought together at a lamination station to create the liquid discharge detection laminate 63. The back sheet can be formed with the holes 64 before the lamination step or after the lamination step. Markers may be used in the manufacturing process in order to properly align a hole 64 with a respective conductive line 61. This laminate 63 forms a precursor to the formation of an absorbent article. Subsequent steps include disposing an absorbent core over the back sheet 60 so as to cover the holes 64 and sandwiching the absorbent core between a top sheet and the back sheet 60.

The conductive lines may be provided by a plurality of conductive threads or wires, such as metal, particularly silver, coated polymer thread or metal wires, such as stainless steel wires. Alternatively, the substrate 62 could be fed into a printing or coating station so as to, for example, apply conductive ink or conductive foils, to the substrate 62, which can then subsequently be fed to a lamination station, in which the substrate 62 is laminated to a backside of back sheet material.

The machine direction feed of the laminate 63 can be formed into a roll for use in making absorbent articles or it can be fed directly into an absorbent article forming process as conventional back sheet material in making the absorbent article.

Thus, in some aspects, an absorbent article has a back sheet with an absorbent core disposed on a body side of the back sheet. On a back side of the back sheet, there is provided a substrate carrying a conductive pattern as a liquid discharge detection circuit that is able to be connected to an electric potential generator for performing liquid discharge detection. At least one or a plurality of holes is formed through the back sheet to communicate portions of the conductive pattern with the absorbent core. Longitudinally adjacent pairs of the revealed portions of the conductive pattern form liquid discharge detection zones for detecting liquid discharge in the absorbent core. The detection zones are longitudinally distributed with respect to the absorbent core.

The outermost revealed portions (and associated holes if a plurality of holes is present) along a longitudinal axis (that is, the frontmost and rearmost revealed portion) can be spaced apart by at least 0.1 L, 0.2 L, 0.3 L, 0.4 L and 0.5 L, wherein L is a total length of the absorbent core along a central longitudinal axis. Additionally or alternatively, a longitudinally adjacent pair of revealed portions disposed closest to a central lateral axis of the absorbent core can be located at a distance from each other of 0.8 L or less, 0.7 L or less, 0.6 L or less and 0.5 L or less. Additionally or alternatively, the liquid discharge detection zones or revealed portions can be distributed over at least 0.5 L, 0.6 L, 0.7 L, 0.8 L and 0.9 L.

In the embodiments of FIGS. 1 and 2, the absorbent core is shown in the form of first and second layers of absorbent cores. This is not necessarily the case. A single integrated absorbent core could be used. The construction of the absorbent core is likewise adaptable in the other embodiments of FIGS. 3 to 5.

In the embodiments of FIGS. 2a-e, 3 and 5, a plurality of holes are provided in the back sheet to reveal underlying conductive portions of liquid discharge sensors. In an alternative embodiment, a fewer number of holes (or just one hole) could be provided to reveal the conductive portions. For example, one can imagine a diagonally oriented hole revealing a part of each of the conductive members in the embodiments of FIGS. 3 and 5 or a longitudinally oriented hole revealing a part of each of the laterally oriented conductive members in the embodiment of FIGS. 2a-e.

The present application has particularly been described with respect to an adult incontinence diaper, and the teachings herein for each of the embodiments can be used in such a diaper. Nonetheless, the liquid discharge detection capability is applicable to a greater range of absorbent articles, such as sanitary towels, baby, toddler and infant diapers and other such absorbent articles where it may be of interest to detect the presence, extent (particularly longitudinal extent), volume or number of liquid discharges. Such information may be of interest for marketing, diagnostic and user care purposes.

The invention claimed is:

1. An absorbent article comprising:
an electrically insulating back sheet;
an absorbent core on a body side of the back sheet;
at least one liquid discharge sensor on a back side of the back sheet; and
at least one hole through the back sheet communicating the at least one liquid discharge sensor with the absorbent core, so that the liquid discharge sensor exhibits a changed electrical property when a part of the absorbent core associated with the liquid discharge sensor through the at least one hole changes from a dry state to a wet state,
wherein the at least one liquid discharge sensor comprises conductive material that is partly communicated with the absorbent core by the at least one hole,
wherein the at least one liquid discharge sensor comprises a plurality of longitudinally extending conductive lines and a plurality of laterally extending conductive lines, wherein each of the laterally extending lines are partly revealed by the at least one hole, and
wherein the at least one liquid discharge sensor is disposed on a carrier sheet or substrate.

2. The absorbent article of claim 1, wherein the liquid discharge sensor is arranged to have first and second spaced conductive paths communicating with the absorbent core through the at least one hole so that when the portion of the absorbent core positioned between the first and second conductive paths changes from a dry state to a wet state, a conductive bridge is formed between the first and second conductive paths that passes through the wet absorbent core.

3. The absorbent article of claim 1, wherein the liquid discharge sensor is arranged to have first and second conductive paths communicating with the absorbent core through a common hole in the back sheet so that when the portion of the absorbent core positioned between the first and second conductive paths changes from a dry state to a wet state, a conductive bridge is formed between the first and second conductive paths that passes through the wet absorbent core in the hole.

4. The absorbent article of claim 1, wherein the liquid discharge sensor is arranged to have first and second conductive paths communicating with the absorbent core through respective holes in the back sheet so that when the portion of the absorbent core positioned between the first and second conductive paths changes from a dry state to a wet state, a conductive bridge is formed between the first and second conductive paths that passes through the wet absorbent core between the holes.

5. The absorbent article of claim 1, comprising a plurality of liquid discharge sensors each capable of determining the presence of a liquid discharge in a respective zone of the absorbent core, and comprising a plurality of holes in the back sheet, each liquid discharge sensor communicating with the absorbent core through at least one hole in the back sheet.

6. The absorbent article of claim 1, comprising a plurality of holes in the back sheet, each hole revealing to the absorbent core an underlying conductive portion of a liquid discharge sensor.

7. The absorbent article of claim 6, wherein a plurality of the holes, or each of the holes, are longitudinally spaced, wherein a longitudinal axis extends in a front to rear direction of the absorbent article.

8. The absorbent article of claim 1, wherein there is a plurality of holes in the back sheet and a plurality of electrically conductive paths that are electrically isolated from one another to form the at least one liquid discharge sensor, wherein each of the holes communicate a respective conductive path with the absorbent core so that current is able to flow from the conductive path in one hole to another conductive path in another hole when the absorbent core is wet.

9. The absorbent article of claim 1, wherein the back sheet, apart from at the at least one hole, otherwise electrically insulates conductive paths forming the at least one liquid discharge sensor from the absorbent core.

10. The absorbent article of claim 1, wherein the total area of the at least one hole is less than 50% of the total area of the absorbent core when the absorbent article is laid out flat and a plan view of the absorbent core is taken.

11. The absorbent article of claim 1, wherein the total area exposed to the absorbent core of conductive paths or lines making up the at least one liquid discharge sensor is less than 50% of the total area of the conductive paths or lines when the absorbent article is laid out flat and the absorbent core is viewed in plan.

12. The absorbent article of claim 11, wherein there is a plurality of longitudinally extending conductive lines that are laterally spaced from one another, wherein a longitudinal axis is in a front to back direction of the absorbent article.

13. The absorbent article of claim 12, wherein there is a respective hole for each of the longitudinal conductive lines.

14. The absorbent article of claim 1, wherein there are a plurality of spaced longitudinal conductive lines connected to a respective lateral conductive line, the lateral conductive lines being longitudinally spaced from one another, the at least one hole revealing part of each of the lateral conductive lines to the absorbent core in order to form the at least one liquid discharge sensor.

15. The absorbent article of claim 14, wherein there is a respective hole revealing a part of the lateral lines.

16. An absorbent article comprising:
an electrically insulating back sheet;
an absorbent core on a body side of the back sheet;
at least one liquid discharge sensor on a back side of the back sheet; and
at least one hole through the back sheet communicating the at least one liquid discharge sensor with the absorbent core, so that the liquid discharge sensor exhibits a changed electrical property when a part of the absorbent core associated with the liquid discharge sensor through the at least one hole changes from a dry state to a wet state, wherein the at least one liquid discharge sensor comprises conductive material that is partly communicated with the absorbent core by the at least one hole,
wherein there is a plurality of conductive lines forming the at least one liquid discharge sensor, each of which lines are partly revealed by the at least one hole,
wherein the at least one liquid discharge sensor is disposed on a carrier sheet or substrate,
wherein the at least one liquid discharge sensor comprises at least one conductive path formed in the shape of an open loop that is able to carry a current around the loop,
wherein the at least one hole reveals to the absorbent core part of an outward leg and part of a return leg, and
wherein if the absorbent core is wet between the exposed part of the legs, then a short circuit will form between the exposed part of the legs as opposed to current flow around the full open loop shaped conductive path.

17. The absorbent article of claim 16, wherein the exposed parts of the outward and return leg are laterally spaced apart.

18. The absorbent article of claim 16, comprising a plurality of longitudinally spaced holes in the back sheet, the holes revealing at least one of the outward leg and the return leg to the absorbent core at longitudinally spaced locations along the loop.

19. The absorbent article of claim 16, comprising first and second such conductive paths that are reverse arranged relative to one another in the longitudinal direction.

20. The absorbent article of claim 19, comprising a plurality of longitudinally spaced holes in the back sheet, the holes revealing at least one of the outward leg and the return leg to the absorbent core at longitudinally spaced locations along the loop, wherein the longitudinally spaced holes respectively reveal to the absorbent core part of the outward leg and the return leg of the first and the second conductive loops.

21. The absorbent article of claim 1, wherein a part of each of a plurality of conductive lines is communicated with the absorbent core by a respective hole in the back sheet.

22. The absorbent article of claim 1, wherein the carrier sheet is attached to the back side or a back face of the back sheet and the absorbent core is disposed on a front face or body side of the back sheet.

23. The absorbent article of claim 1, wherein the combination of the carrier sheet and the back sheet is part of a liquid impermeable back liner, which is liquid impermeable, disposed over a back side of the carrier sheet to prevent liquid discharge passing therethrough.

24. The absorbent article of claim 1, wherein the back sheet is made of a liquid impermeable material, and wherein the back sheet is at least part of a back liner of a diaper.

25. The absorbent article of claim 1, wherein the absorbent article also includes a liquid permeable body side liner, wherein the absorbent core is sandwiched between the back sheet and the body side liner.

26. The absorbent article of claim 1, wherein the at least one liquid discharge sensor is made up of a plurality of conductive members printed, coated or adhered to a body side surface of a substrate.

27. The absorbent article of claim 1, including a plurality of conductive leads extending from the at least one liquid discharge sensor to a common contact area, wherein the leads are covered by the back sheet.

28. An absorbent article comprising:
an electrically insulating back sheet;
an absorbent core on a body side of the back sheet;
at least one liquid discharge sensor on a back side of the back sheet; and
at least one hole through the back sheet communicating the at least one liquid discharge sensor with the absorbent core, so that the liquid discharge sensor exhibits a changed electrical property when a part of the absorbent core associated with the liquid discharge sensor through the at least one hole changes from a dry state to a wet state,
wherein the at least one liquid discharge sensor comprises conductive material that is partly communicated with the absorbent core by the at least one hole,
wherein there is a plurality of conductive lines forming the at least one liquid discharge sensor, each of which lines are partly revealed by the at least one hole,
wherein the at least one liquid discharge sensor is disposed on a carrier sheet or substrate,
wherein a plurality of conductive lines are disposed on a first electrically insulating layer forming the carrier sheet or substrate that are partially covered by the back sheet,
wherein portions of the conductive lines exposed by the at least one hole in the back sheet are in electrical communication with the absorbent core, thereby providing electrodes of the at least one liquid discharge sensor, and
wherein portions of the conductive lines covered by the back sheet include leads extending between each electrode and a control unit attachment area, the back sheet ensuring the leads are electrically insulated from the absorbent core, wherein the electrodes are arranged so that a plurality of longitudinally spaced liquid detection zones are provided, each detection zone defined between a pair of electrodes that are electrically isolated from one another when the absorbent core is dry and which are arranged so that when the control unit connects an electric potential to corresponding leads and when the absorbent core is wet, a conductive bridge is formed between the pair of electrodes by the wet absorbent core, wherein a longitudinal axis extends in a front to rear direction of the absorbent article when worn.

29. The absorbent article of claim 28, wherein the electrodes are elongate and laterally oriented, the leads are elongate and longitudinally oriented, and the at least one hole in the back sheet includes a plurality of laterally oriented elongate holes forming windows exposing the conductive lines to form each of the electrodes.

30. The absorbent article of claim 1, wherein the back sheet provides a frame of insulating material around a conductive portion of the liquid discharge sensor exposed by the at least one hole.

31. The absorbent article of claim 1, wherein the at least one hole in the back sheet includes a plurality of holes in the back sheet that form windows exposing portions of conductive lines or members to the absorbent core to form a plurality of liquid discharge sensors, wherein the windows are longitudinally spaced so as to form respective liquid discharge sensors between longitudinally spaced pairs of exposed portions of the conductive lines or members.

32. The absorbent article of claim 1, wherein conductive lines or members making up the at least one liquid discharge sensor extend to the at least one hole on one side of the at least one hole, bridge the at least one hole and continue to extend from the at least one hole on an opposed side of the at least one hole.

33. The absorbent article of claim 1, wherein the at least one liquid discharge sensor comprises a plurality of longitudinally spaced conductive members that are in communication with the absorbent core through the at least one hole, wherein the front most conductive member communicating with the absorbent core and the rear most conductive member communicating with the absorbent core along the front to rear longitudinal axis of the absorbent core are located a distance apart of at least 0.1 L, wherein L is a total longitudinal length of the absorbent core when the absorbent article is laid out flat and viewed in plan.

34. The absorbent article of claim 1, wherein the at least one liquid discharge sensor comprises at least one pair of longitudinally adjacent conductive members communicating with the absorbent core through the at least one hole, wherein the pair of adjacent conductive members are located a distance apart of less than or equal to 0.8 L, wherein L is a total longitudinal length of the absorbent core when the absorbent article is laid out flat and viewed in plan.

35. The absorbent article of claim 1, wherein the at least one liquid discharge sensor comprises a plurality of liquid discharge sensors that are longitudinally distributed over at least 0.5 L, wherein L is a total length of the absorbent core when viewed in plan when the absorbent article is laid out flat.

36. An absorbent article comprising:
an electrically insulating back sheet;
an absorbent core on a body side of the back sheet;
at least one liquid discharge sensor on a back side of the back sheet, and
a plurality of holes through the back sheet communicating the at least one liquid discharge sensor with the absorbent core, so that the liquid discharge sensor exhibits a changed electrical property when a part of the absorbent core associated with the liquid discharge sensor through at least one of the plurality of holes changes from a dry state to a wet state,
wherein the at least one liquid discharge sensor comprises conductive material that is partly communicated with the absorbent core by at least one of the plurality of holes,
wherein the at least one liquid discharge sensor comprises a plurality of conductive lines, each of which lines are partly revealed by at least one of the plurality of holes,
wherein the at least one liquid discharge sensor is disposed on a carrier sheet or substrate, and
wherein each of the holes of the plurality of holes is longitudinally spaced along a longitudinal axis from each of the other of the plurality of holes, the longitudinal axis extending in a front to rear direction of the absorbent article.

\* \* \* \* \*